United States Patent
Endell et al.

(10) Patent No.: US 10,617,691 B2
(45) Date of Patent: Apr. 14, 2020

(54) COMBINATION OF AN ANTI-CD19 ANTIBODY AND A BRUTON'S TYROSINE KINASE INHIBITOR AND USES THEREOF

(71) Applicant: MORPHOSYS AG, Planegg (DE)

(72) Inventors: Jan Endell, Munich (DE); Rainer Boxhammer, Aying (DE); Mark Winderlich, Munich (DE)

(73) Assignee: MORPHOSYS AG, Planegg (DE)

( * ) Notice: Subject to any disclaimer, the term of this patent is extended or adjusted under 35 U.S.C. 154(b) by 41 days.

(21) Appl. No.: 15/572,914

(22) PCT Filed: May 25, 2016

(86) PCT No.: PCT/EP2016/061744
§ 371 (c)(1),
(2) Date: Nov. 9, 2017

(87) PCT Pub. No.: WO2016/189014
PCT Pub. Date: Dec. 1, 2016

(65) Prior Publication Data
US 2018/0153892 A1  Jun. 7, 2018

(30) Foreign Application Priority Data

May 26, 2015 (EP) .................... 15169124
Nov. 27, 2015 (EP) .................... 15196860

(51) Int. Cl.
| | | |
|---|---|---|
| *A61K 31/519* | (2006.01) | |
| *A61K 39/395* | (2006.01) | |
| *C07K 16/28* | (2006.01) | |
| *A61K 47/68* | (2017.01) | |
| *A61P 35/00* | (2006.01) | |
| *A61K 39/00* | (2006.01) | |

(52) U.S. Cl.
CPC ...... *A61K 31/519* (2013.01); *A61K 39/39558* (2013.01); *A61K 47/68* (2017.08); *A61P 35/00* (2018.01); *C07K 16/2803* (2013.01); *C07K 16/2896* (2013.01); *A61K 2039/505* (2013.01); *C07K 2317/24* (2013.01); *C07K 2317/732* (2013.01)

(58) Field of Classification Search
None
See application file for complete search history.

(56) References Cited

U.S. PATENT DOCUMENTS

| | | | |
|---|---|---|---|
| 5,686,072 A | 11/1997 | Uhr et al. | 424/183.1 |
| 7,109,304 B2 | 9/2006 | Hansen et al. | 530/387.3 |
| 7,514,444 B2 | 4/2009 | Honigberg et al. | 514/263.22 |
| 7,902,338 B2 | 3/2011 | Hansen et al. | 530/387.1 |
| 8,008,309 B2 | 8/2011 | Honigberg et al. | 514/262.1 |
| 8,097,703 B2 | 1/2012 | Rao-Naik et al. | 530/387.1 |
| 8,697,711 B2 | 4/2014 | Honigberg et al. | 514/262.1 |
| 8,735,403 B2 | 5/2014 | Honigberg et al. | 514/262.1 |
| 8,754,090 B2 | 6/2014 | Buggy et al. | 514/262.1 |
| 8,957,079 B2 | 2/2015 | Honigberg et al. | 514/262.1 |
| 2007/0154473 A1 | 7/2007 | Super et al. | 424/133.1 |

FOREIGN PATENT DOCUMENTS

| | | |
|---|---|---|
| WO | WO2002022212 | 3/2002 |
| WO | WO2005012493 | 2/2005 |
| WO | WO2007002223 | 1/2007 |
| WO | WO2007076950 | 7/2007 |
| WO | WO2008022152 | 2/2008 |
| WO | WO2008031056 | 3/2008 |
| WO | WO2008150494 | 12/2008 |
| WO | WO2009052431 | 4/2009 |
| WO | WO2010053716 | 5/2010 |
| WO | WO2010095031 | 8/2010 |
| WO | WO2010151341 | 12/2010 |
| WO | WO2011147834 | 12/2011 |
| WO | WO2012010561 | 1/2012 |
| WO | WO2012010562 | 1/2012 |
| WO | WO2012156455 | 11/2012 |
| WO | WO2013024095 | 2/2013 |
| WO | WO2013024097 | 2/2013 |

OTHER PUBLICATIONS

Wu et al. (Journal of Hematology and Oncology 2013, 6:36) (Year: 2013).*
Anderson et al. "Expression of human B cell-associated antigens on leukemias and lymphomas: a model of human B cell differentiation" Blood 1984 63:1424-1433.
Burger et al. "Ibrutinib plus rituximab for patients with high risk chronic lymphocytic leukaemia: a single-arm, phase 2 study" Lancet Oncol. 2014 15(19):1090-1099.
Duong et al. "Effect of kinase inhibitors on the therapeutic properties of monoclonal antibodies" mAbs 2015 192-198.
Fraietta et al. "Ibrutinib enhances chimeric antigen receptor T-cell engraftment and efficacy in leukemia" Blood 2016 127(9):1117-1127.
Grossbard et al. "Anti-B4-blocked ricin: a phase II trial of 7 day continuous infusion in patients with multiple myeloma" Br. J. Haematol 1998 102:509-15.
Kalos et al. "T cells with Chimeric Antigen Receptors Have Potent Antitumor Effects and Can Establish Memory in Patients with Advanced Leukemia" Science Translational Medicine 2011 3 (95):1-11.
Kohrt et al. "Ibrutinib antagonizes rituximab-dependent NK cell-mediated cytotoxicity" Blood 2014 123:1957-1960.
Loken et al. "Flow cytometric analysis of human bone marrow. II. Normal B lymphocyte development" Blood 1987 70:1316-1324.
Nadler et al. "B4, a human B lymphocyte-associated antigen expressed on normal, mitogen-activated, and malignant B lymphocytes" J. Immunol. 1983 131:244-250.
Robak et al. "Antibody therapy alone and in combination with targeted drugs in chronic lymphocytic leukemia" Seminar in Oncology 2016 43:280-290.

(Continued)

Primary Examiner — Meera Natarajan
(74) Attorney, Agent, or Firm — Licata & Tyrrell P.C.

(57) ABSTRACT

The present disclosure describes a pharmaceutical combination of an anti-CD19 antibody and a Bruton's tyrosine kinase (BTK) inhibitor for the treatment of non-Hodgkin's lymphoma, chronic lymphocytic leukemia and/or acute lymphoblastic leukemia.

16 Claims, 20 Drawing Sheets

Specification includes a Sequence Listing.

(56) References Cited

OTHER PUBLICATIONS

Ruella et al. "Combination of Ibrutinib and Anti-CD19 Chimeric Antigen Receptor T Cells for the Treatment of Relapsing/Refractory Mantel Cell Lymphoma (MCL)" 20th Congress of the European Hematology Association Jun. 13, 2015, p. 1.
Sadelain et al. "The promise and potential pitfalls of chimeric antigen receptors" Current Opinion in Immunology 2009 21(2):215-223.
Scheuermann, R.H. and racial, E. "CD19 antigen in leukemia and lymphoma diagnosis and immunotherapy" Leukemia & Lymphoma 1995 18:385-397.
Treon et al. "Expression of serotherapy target antigens in Waldenstrom's macroglobulinemia: therapeutic applications and considerations" Semin. Oncol. 2003 30:248-52.
Uckun et al. "Detailed studies on expression and function of CD19 surface determinant by using B43 monoclonal antibody and the clinical potential of anti-CD19 immunotoxins" Blood 1988 71:13-29.
Woyach et al. "2894 Final results of a Phase I Study of the Fc Engineered CD19 Antibody XmAb®,5574 (MOR00208) in patients with relapsed or refractory chronic lymphocytic leukemia (CLL) or small lymphocytic lymphoma (SLL)" URL:http://ash.confex.com/ash/2012/webprogra/Paer51418.html Dec. 9, 2012.
Woyach et al. "A phase 1 trial of the Fc-engineered CD19 antibody XmAb5574 (MOR00208) demonostrates safety and preliminary efficacy in relapsed CLL" Blood 2014 124(24):3553-3560.
Wu et al. "Novel agents for chronic lymphocytic leukemia" Journal of Hematology & Oncology 2013 6:36.
"Study to Evaluate Efficacy and Safety of Mor208 with Idelailsib in R/R CLL/SLL Patients Pretreated with BTKi" ClinicalTrials.gov 2015.
Efficacy and Safety Study of PCI-32765 Combine with Ofatumumab in CLL (PCYC-1109-CA) ClinicalTrials.gov 2010.
International Search Report and Written Opinion in PCT/EP2016/061744 dated Jul. 21, 2016.
International Preliminary Report on Patentability in PCT/EP2016/061744 dated Nov. 28, 2017.
Extended European Search Report in EP Patent Application No. 19192976.9-1111 dated Nov. 5, 2019.
Office Action and Search Report from Russian Federation in RU Patent Application No. 2017143166/10 dated Nov. 28, 2019 with English translations.
Horton et al. "Potent in vitro and in vivo Activity of an Fc-Engineered Anti-CD19 Monoclonal Antibody against Lymphoma and Leukemia" Cancer Res. 2008 68(19): 8049-57.
Robak, T. "Current and emerging monoclonal antibody treatments for chronic lymphocytic leukemia: state of the art" Expert Reviews of Hematology 2014 7(6):841-857.
Savchenko et al. "Klinicheskie rekomendacii po obsledovaniyu i lecheniya bolnykh khonicheskim leikozom" II Kongress gematologov 2014 pp. 1-23 with English translation.

* cited by examiner

Cytotoxicity of MOR00208 and Ibrutinib alone and in combination in Ramos cell line Cytotoxicity of MOR00208 and Ibrutinib alone and in combination in MEC-1 cell line Cytotoxicity of MOR00208 and Ibrutinib alone and in combination in MEC-1 cell line

Figure 4

The amino acid sequence of the MOR00208 Variable Heavy Domain is:
(The CDRs are bolded and underlined)

EVQLVESGGGLVKPGGSLKLSCAASGYTFTSYVMHWVRQAPGKGLEWIGYINPY NDGTKYNEKFQGRVTISSDKSISTAYMELSSLRSEDTAMYYCARGTYYYGTRVFDYWG QGTLVTVSS (SEQ ID NO: 10)

The amino acid sequence of the MOR00208 Variable Light Domain is:
(The CDRs are bolded and underlined)

DIVMTQSPATLSLSPGERATLSCRSSKSLQNVNGNTYLYWFQQKPGQSPQLLIYR MSNLNSGVPDRFSGSGSGTEFTLTISSLEPEDFAVYYCMQHLEYPITFGAGTKLEIK (SEQ ID NO: 11)

The amino acid sequence of the MOR00208 HCDR1 is: SYVMH (SEQ ID NO: 1)

The amino acid sequence of the MOR00208 HCDR2 is: NPYNDG (SEQ ID NO: 2)

The amino acid sequence of the MOR00208 HCDR3 is: GTYYYGTRVFDY (SEQ ID NO: 3)

The amino acid sequence of the MOR00208 LCDR1 is: RSSKSLQNVNGNTYLY (SEQ ID NO: 4)

The amino acid sequence of the MOR00208 LCDR2 is: RMSNLNS (SEQ ID NO: 5)

The amino acid sequence of the MOR00208 LCDR3 is: MQHLEYPIT (SEQ ID NO: 6)

Figure 5

Sequence of Fc regions

The amino acids sequence of the MOR00208 heavy chain Fc region is:

ASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKKVEPKSCDKTHTCPPCPAPELLGG
PDVFLFPPKPKDTLMISRTPEVTCVVVDVSHEDPEVQFNWYVDGVEVHNAKTKPREEQF
NSTFRVVSVLTVVHQDWLNGKEYKCKVSNKALPAPEEKTISKTKGQPREPQVYTLPPSRE
EMTKNQVSLTCLVKGFYPSDIAVEWESNGQPENNYKTTPPMLDSDGSFFLYSKLTVDKSR
WQQGNVFSCSVMHEALHNHYTQKSLSLSPGK (SEQ ID NO: 12).

The amino acids sequence of the MOR00208 light chain Fc region is:

RTVAAPSVFIFPPSDEQLKSGTASVVCLLNNFYPREAKVQWKVDNALQSGNSQESVTEQ
DSKD STYSLSSTLTLSKADYEKHKVYACEVTHQGLSSPVTKSFNRGEC (SEQ ID NO: 13)

Cytotoxicity of MOR00208 and Ibrutinib alone and in combination in MEC-1 cell line Cytotoxicity of MOR00208 and Ibrutinib alone and in combination in MEC-1 cell line Cytotoxicity of MOR00208 and Ibrutinib alone and in combination in MEC-1 cell line Chou Talay CI curves Chou Talay CI curves Chou Talay CI curves Graphical representation of Clarke analysis in Table 10 of the data shown in Table 1

Graphical representation of Clarke analysis in Table 11 of the data shown in Table 2

Graphical representation of Clarke analysis in Table 12 of the data shown in Table 3

Graphical representation of Clarke analysis in Table 13 of the data shown in Table 4

Graphical representation of Clarke analysis in Table 14 of the data shown in Table 5

Graphical representation of Clarke analysis in Table 15 of the data shown in Table 6

Graphical representation of Clarke analysis in Table 16 of the data shown in Table 7

Graphical representation of Clarke analysis in Table 17 of the data shown in Table 8

Graphical representation of Clarke analysis in Table 18 of the data shown in Table 9

SEQUENCE LISTING

```
<160> NUMBER OF SEQ ID NOS: 15

<210> SEQ ID NO 1
<211> LENGTH: 5
<212> TYPE: PRT
<213> ORGANISM: Artificial sequence
<220> FEATURE:
<223> OTHER INFORMATION: synthetic construct

<400> SEQUENCE: 1

Ser Tyr Val Met His
1               5

<210> SEQ ID NO 2
<211> LENGTH: 6
<212> TYPE: PRT
<213> ORGANISM: Artificial sequence
<220> FEATURE:
<223> OTHER INFORMATION: synthetic construct

<400> SEQUENCE: 2

Asn Pro Tyr Asn Asp Gly
1               5

<210> SEQ ID NO 3
<211> LENGTH: 12
<212> TYPE: PRT
<213> ORGANISM: Artificial sequence
<220> FEATURE:
<223> OTHER INFORMATION: synthetic construct

<400> SEQUENCE: 3

Gly Thr Tyr Tyr Tyr Gly Thr Arg Val Phe Asp Tyr
1               5                   10

<210> SEQ ID NO 4
<211> LENGTH: 16
<212> TYPE: PRT
<213> ORGANISM: Artificial sequence
<220> FEATURE:
<223> OTHER INFORMATION: synthetic construct

<400> SEQUENCE: 4

Arg Ser Ser Lys Ser Leu Gln Asn Val Asn Gly Asn Thr Tyr Leu Tyr
1               5                   10                  15

<210> SEQ ID NO 5
<211> LENGTH: 7
<212> TYPE: PRT
<213> ORGANISM: Artificial sequence
<220> FEATURE:
<223> OTHER INFORMATION: synthetic construct

<400> SEQUENCE: 5

Arg Met Ser Asn Leu Asn Ser
1               5
```

-continued

```
<210> SEQ ID NO 6
<211> LENGTH: 9
<212> TYPE: PRT
<213> ORGANISM: Artificial sequence
<220> FEATURE:
<223> OTHER INFORMATION: synthetic construct

<400> SEQUENCE: 6

Met Gln His Leu Glu Tyr Pro Ile Thr
1               5

<210> SEQ ID NO 7
<211> LENGTH: 556
<212> TYPE: PRT
<213> ORGANISM: Homo sapiens
<220> FEATURE:
<223> OTHER INFORMATION: CD19

<400> SEQUENCE: 7

Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
            20                  25                  30

Asn Ala Val Leu Gln Cys Leu Lys Gly Thr Ser Asp Gly Pro Thr Gln
        35                  40                  45

Gln Leu Thr Trp Ser Arg Glu Ser Pro Leu Lys Pro Phe Leu Lys Leu
    50                  55                  60

Ser Leu Gly Leu Pro Gly Leu Gly Ile His Met Arg Pro Leu Ala Ile
65                  70                  75                  80

Trp Leu Phe Ile Phe Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
            100                 105                 110

Val Asn Val Glu Gly Ser Gly Glu Leu Phe Arg Trp Asn Val Ser Asp
        115                 120                 125

Leu Gly Gly Leu Gly Cys Gly Leu Lys Asn Arg Ser Ser Glu Gly Pro
    130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Leu Pro Pro
                165                 170                 175

Arg Asp Ser Leu Asn Gln Ser Leu Ser Gln Asp Leu Thr Met Ala Pro
            180                 185                 190

Gly Ser Thr Leu Trp Leu Ser Cys Gly Val Pro Pro Asp Ser Val Ser
        195                 200                 205

Arg Gly Pro Leu Ser Trp Thr His Val His Pro Lys Gly Pro Lys Ser
    210                 215                 220

Leu Leu Ser Leu Glu Leu Lys Asp Asp Arg Pro Ala Arg Asp Met Trp
225                 230                 235                 240

Val Met Glu Thr Gly Leu Leu Leu Pro Arg Ala Thr Ala Gln Asp Ala
                245                 250                 255

Gly Lys Tyr Tyr Cys His Arg Gly Asn Leu Thr Met Ser Phe His Leu
            260                 265                 270

Glu Ile Thr Ala Arg Pro Val Leu Trp His Trp Leu Leu Arg Thr Gly
        275                 280                 285

Gly Trp Lys Val Ser Ala Val Thr Leu Ala Tyr Leu Ile Phe Cys Leu
    290                 295                 300
```

Cys Ser Leu Val Gly Ile Leu His Leu Gln Arg Ala Leu Val Leu Arg
305                 310                 315                 320

Arg Lys Arg Lys Arg Met Thr Asp Pro Thr Arg Phe Phe Lys Val
            325                 330                 335

Thr Pro Pro Pro Gly Ser Gly Pro Gln Asn Gln Tyr Gly Asn Val Leu
            340                 345                 350

Ser Leu Pro Thr Pro Thr Ser Gly Leu Gly Arg Ala Gln Arg Trp Ala
            355                 360                 365

Ala Gly Leu Gly Gly Thr Ala Pro Ser Tyr Gly Asn Pro Ser Ser Asp
370                 375                 380

Val Gln Ala Asp Gly Ala Leu Gly Ser Arg Ser Pro Pro Gly Val Gly
385                 390                 395                 400

Pro Glu Glu Glu Glu Gly Glu Gly Tyr Glu Glu Pro Asp Ser Glu Glu
                405                 410                 415

Asp Ser Glu Phe Tyr Glu Asn Asp Ser Asn Leu Gly Gln Asp Gln Leu
                420                 425                 430

Ser Gln Asp Gly Ser Gly Tyr Glu Asn Pro Glu Asp Glu Pro Leu Gly
            435                 440                 445

Pro Glu Asp Glu Asp Ser Phe Ser Asn Ala Glu Ser Tyr Glu Asn Glu
450                 455                 460

Asp Glu Glu Leu Thr Gln Pro Val Ala Arg Thr Met Asp Phe Leu Ser
465                 470                 475                 480

Pro His Gly Ser Ala Trp Asp Pro Ser Arg Glu Ala Thr Ser Leu Gly
                485                 490                 495

Ser Gln Ser Tyr Glu Asp Met Arg Gly Ile Leu Tyr Ala Ala Pro Gln
            500                 505                 510

Leu Arg Ser Ile Arg Gly Gln Pro Gly Pro Asn His Glu Glu Asp Ala
            515                 520                 525

Asp Ser Tyr Glu Asn Met Asp Asn Pro Asp Gly Pro Asp Pro Ala Trp
            530                 535                 540

Gly Gly Gly Gly Arg Met Gly Thr Trp Ser Thr Arg
545                 550                 555

<210> SEQ ID NO 8
<211> LENGTH: 450
<212> TYPE: PRT
<213> ORGANISM: Artificial sequence
<220> FEATURE:
<223> OTHER INFORMATION: Heavy chain RefMab33

<400> SEQUENCE: 8

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ala
                20                  25                  30

Gly Met Ser Val Gly Trp Ile Arg Gln Pro Pro Gly Lys Ala Leu Glu
            35                  40                  45

Trp Leu Ala Asp Ile Trp Trp Asp Asp Lys Lys His Tyr Asn Pro Ser
    50                  55                  60

Leu Lys Asp Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Asp Met Ile Phe Asn Phe Tyr Phe Asp Val Trp Gly Gln
            100                 105                 110

Gly Thr Thr Val Thr Val Ser Ala Ser Thr Lys Gly Pro Ser Val
            115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Asp Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Gln Phe Asn Trp Tyr Val Asp Gly Val Glu Val His
            275                 280                 285

Asn Ala Lys Thr Lys Pro Arg Glu Glu Gln Phe Asn Ser Thr Phe Arg
290                 295                 300

Val Val Ser Val Leu Thr Val Val His Gln Asp Trp Leu Asn Gly Lys
305                 310                 315                 320

Glu Tyr Lys Cys Lys Val Ser Asn Lys Ala Leu Pro Ala Pro Glu Glu
                325                 330                 335

Lys Thr Ile Ser Lys Thr Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Met
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
450

<210> SEQ ID NO 9
<211> LENGTH: 213
<212> TYPE: PRT
<213> ORGANISM: Artificial sequence
<220> FEATURE:
<223> OTHER INFORMATION: Light chain RefMab33

<400> SEQUENCE: 9

Asp Ile Gln Met Thr Gln Ser Pro Ser Thr Leu Ser Ala Ser Val Gly
1               5                   10                  15

```
Asp Arg Val Thr Ile Thr Cys Ser Ala Ser Ser Arg Val Gly Tyr Met
            20                  25                  30

His Trp Tyr Gln Gln Lys Pro Gly Lys Ala Pro Lys Leu Leu Ile Tyr
            35                  40                  45

Asp Thr Ser Lys Leu Ala Ser Gly Val Pro Ser Arg Phe Ser Gly Ser
 50                  55                  60

Gly Ser Gly Thr Glu Phe Thr Leu Thr Ile Ser Ser Leu Gln Pro Asp
 65                  70                  75                  80

Asp Phe Ala Thr Tyr Tyr Cys Phe Gln Gly Ser Gly Tyr Pro Phe Thr
                 85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys
    210

<210> SEQ ID NO 10
<211> LENGTH: 121
<212> TYPE: PRT
<213> ORGANISM: Artificial sequence
<220> FEATURE:
<223> OTHER INFORMATION: synthetic construct

<400> SEQUENCE: 10

Glu Val Gln Leu Val Glu Ser Gly Gly Gly Leu Val Lys Pro Gly Gly
1               5                   10                  15

Ser Leu Lys Leu Ser Cys Ala Ala Ser Gly Tyr Thr Phe Thr Ser Tyr
            20                  25                  30

Val Met His Trp Val Arg Gln Ala Pro Gly Lys Gly Leu Glu Trp Ile
            35                  40                  45

Gly Tyr Ile Asn Pro Tyr Asn Asp Gly Thr Lys Tyr Asn Glu Lys Phe
 50                  55                  60

Gln Gly Arg Val Thr Ile Ser Ser Asp Lys Ser Ile Ser Thr Ala Tyr
 65                  70                  75                  80

Met Glu Leu Ser Ser Leu Arg Ser Glu Asp Thr Ala Met Tyr Tyr Cys
                 85                  90                  95

Ala Arg Gly Thr Tyr Tyr Tyr Gly Thr Arg Val Phe Asp Tyr Trp Gly
            100                 105                 110

Gln Gly Thr Leu Val Thr Val Ser Ser
            115                 120

<210> SEQ ID NO 11
<211> LENGTH: 112
<212> TYPE: PRT
<213> ORGANISM: Artificial sequence
<220> FEATURE:
```

<223> OTHER INFORMATION: synthetic construct

<400> SEQUENCE: 11

```
Asp Ile Val Met Thr Gln Ser Pro Ala Thr Leu Ser Leu Ser Pro Gly
1               5                   10                  15

Glu Arg Ala Thr Leu Ser Cys Arg Ser Ser Lys Ser Leu Gln Asn Val
            20                  25                  30

Asn Gly Asn Thr Tyr Leu Tyr Trp Phe Gln Gln Lys Pro Gly Gln Ser
        35                  40                  45

Pro Gln Leu Leu Ile Tyr Arg Met Ser Asn Leu Asn Ser Gly Val Pro
    50                  55                  60

Asp Arg Phe Ser Gly Ser Gly Ser Gly Thr Glu Phe Thr Leu Thr Ile
65                  70                  75                  80

Ser Ser Leu Glu Pro Glu Asp Phe Ala Val Tyr Tyr Cys Met Gln His
                85                  90                  95

Leu Glu Tyr Pro Ile Thr Phe Gly Ala Gly Thr Lys Leu Glu Ile Lys
            100                 105                 110
```

<210> SEQ ID NO 12
<211> LENGTH: 330
<212> TYPE: PRT
<213> ORGANISM: Artificial sequence
<220> FEATURE:
<223> OTHER INFORMATION: synthetic construct

<400> SEQUENCE: 12

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Asp Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Gln Phe Asn Trp
145                 150                 155                 160

Tyr Val Asp Gly Val Glu Val His Asn Ala Lys Thr Lys Pro Arg Glu
                165                 170                 175

Glu Gln Phe Asn Ser Thr Phe Arg Val Val Ser Val Leu Thr Val Val
            180                 185                 190

His Gln Asp Trp Leu Asn Gly Lys Glu Tyr Lys Cys Lys Val Ser Asn
        195                 200                 205

Lys Ala Leu Pro Ala Pro Glu Glu Lys Thr Ile Ser Lys Thr Lys Gly
    210                 215                 220

Gln Pro Arg Glu Pro Gln Val Tyr Thr Leu Pro Pro Ser Arg Glu Glu
225                 230                 235                 240
```

Met Thr Lys Asn Gln Val Ser Leu Thr Cys Leu Val Lys Gly Phe Tyr
              245                 250                 255

Pro Ser Asp Ile Ala Val Glu Trp Glu Ser Asn Gly Gln Pro Glu Asn
              260                 265                 270

Asn Tyr Lys Thr Thr Pro Pro Met Leu Asp Ser Asp Gly Ser Phe Phe
              275                 280                 285

Leu Tyr Ser Lys Leu Thr Val Asp Lys Ser Arg Trp Gln Gln Gly Asn
              290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
              325                 330

<210> SEQ ID NO 13
<211> LENGTH: 107
<212> TYPE: PRT
<213> ORGANISM: Artificial sequence
<220> FEATURE:
<223> OTHER INFORMATION: synthetic construct

<400> SEQUENCE: 13

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
              20                  25                  30

Tyr Pro Arg Glu Ala Lys Val Gln Trp Lys Val Asp Asn Ala Leu Gln
              35                  40                  45

Ser Gly Asn Ser Gln Glu Ser Val Thr Glu Gln Asp Ser Lys Asp Ser
       50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                  85                  90                  95

Pro Val Thr Lys Ser Phe Asn Arg Gly Glu Cys
              100                 105

<210> SEQ ID NO 14
<211> LENGTH: 451
<212> TYPE: PRT
<213> ORGANISM: Artificial sequence
<220> FEATURE:
<223> OTHER INFORMATION: synthetic construct

<400> SEQUENCE: 14

Glu Val Gln Leu Val Glu Ser Gly Gly Gly Leu Val Lys Pro Gly Gly
1               5                   10                  15

Ser Leu Lys Leu Ser Cys Ala Ala Ser Gly Tyr Thr Phe Thr Ser Tyr
              20                  25                  30

Val Met His Trp Val Arg Gln Ala Pro Gly Lys Gly Leu Glu Trp Ile
              35                  40                  45

Gly Tyr Ile Asn Pro Tyr Asn Asp Gly Thr Lys Tyr Asn Glu Lys Phe
       50                  55                  60

Gln Gly Arg Val Thr Ile Ser Ser Asp Lys Ser Ile Ser Thr Ala Tyr
65                  70                  75                  80

Met Glu Leu Ser Ser Leu Arg Ser Glu Asp Thr Ala Met Tyr Tyr Cys
                  85                  90                  95

Ala Arg Gly Thr Tyr Tyr Tyr Gly Thr Arg Val Phe Asp Tyr Trp Gly

```
                    100                 105                 110
Gln Gly Thr Leu Val Thr Val Ser Ser Ala Ser Thr Lys Gly Pro Ser
                115                 120                 125

Val Phe Pro Leu Ala Pro Ser Ser Lys Ser Thr Ser Gly Gly Thr Ala
            130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Asp Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Phe Asn Ser Thr Phe
    290                 295                 300

Arg Val Val Ser Val Leu Thr Val His Gln Asp Trp Leu Asn Gly
305                 310                 315                 320

Lys Glu Tyr Lys Cys Lys Val Ser Asn Lys Ala Leu Pro Ala Pro Glu
                325                 330                 335

Glu Lys Thr Ile Ser Lys Thr Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Met Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 15
<211> LENGTH: 219
<212> TYPE: PRT
<213> ORGANISM: Artificial sequence
<220> FEATURE:
<223> OTHER INFORMATION: synthetic construct

<400> SEQUENCE: 15

Asp Ile Val Met Thr Gln Ser Pro Ala Thr Leu Ser Leu Ser Pro Gly
```

```
1               5                   10                  15
Glu Arg Ala Thr Leu Ser Cys Arg Ser Ser Lys Ser Leu Gln Asn Val
            20                  25                  30

Asn Gly Asn Thr Tyr Leu Tyr Trp Phe Gln Gln Lys Pro Gly Gln Ser
            35                  40                  45

Pro Gln Leu Leu Ile Tyr Arg Met Ser Asn Leu Asn Ser Gly Val Pro
    50                  55                  60

Asp Arg Phe Ser Gly Ser Gly Ser Gly Thr Glu Phe Thr Leu Thr Ile
65                  70                  75                  80

Ser Ser Leu Glu Pro Glu Asp Phe Ala Val Tyr Tyr Cys Met Gln His
            85                  90                  95

Leu Glu Tyr Pro Ile Thr Phe Gly Ala Gly Thr Lys Leu Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
            130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
            165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
            210                 215
```

COMBINATION OF AN ANTI-CD19 ANTIBODY AND A BRUTON'S TYROSINE KINASE INHIBITOR AND USES THEREOF

This patent application is the U.S. National Stage of International Application No. PCT/EP2016/061744 filed May 25, 2016, which claims the benefit of EP 15196860.9 filed Nov. 27, 2015 and EP 15169124.3 filed May 26, 2015, each of which is incorporated by reference in its entirety.

FIELD OF THE INVENTION

The present disclosure is related to a pharmaceutical combination of an anti-CD19 antibody and a Bruton's tyrosine kinase (BTK) inhibitor for the treatment of non-Hodgkin's lymphoma, chronic lymphocytic leukemia and/or acute lymphoblastic leukemia.

BACKGROUND

B cells are lymphocytes that play a large role in the humoral immune response. They are produced in the bone marrow of most mammals, and represent 5-15% of the circulating lymphoid pool. The principal function of B cells is to make antibodies against various antigens, and are an essential component of the adaptive immune system.

Because of their critical role in regulating the immune system, disregulation of B cells is associated with a variety of disorders, such as lymphomas, and leukemias. These include non-Hodgkin's lymphoma (NHL), chronic lymphocytic leukemia (CLL) and acute lymphoblastic leukemia (ALL).

NHL is a heterogeneous malignancy originating from lymphocytes. In the United States (U.S.), the incidence is estimated at 65,000/year with mortality of approximately 20,000 (American Cancer Society, 2006; and SEER Cancer Statistics Review). The disease can occur in all ages, the usual onset begins in adults over 40 years, with the incidence increasing with age. NHL is characterized by a clonal proliferation of lymphocytes that accumulate in the lymph nodes, blood, bone marrow and spleen, although any major organ may be involved. The current classification system used by pathologists and clinicians is the World Health Organization (WHO) Classification of Tumours, which organizes NHL into precursor and mature B-cell or T-cell neoplasms. The PDQ is currently dividing NHL as indolent or aggressive for entry into clinical trials. The indolent NHL group is comprised primarily of follicular subtypes, small lymphocytic lymphoma, MALT (mucosa-associated lymphoid tissue), and marginal zone; indolent encompasses approximately 50% of newly diagnosed B-cell NHL patients. Aggressive NHL includes patients with histologic diagnoses of primarily diffuse large B cell (DLBL, DLBCL, or DLCL) (40% of all newly diagnosed patients have diffuse large cell), Burkitt's, and mantle cell. The clinical course of NHL is highly variable. A major determinant of clinical course is the histologic subtype. Most indolent types of NHL are considered to be incurable disease. Patients respond initially to either chemotherapy or antibody therapy and most will relapse. Studies to date have not demonstrated an improvement in survival with early intervention. In asymptomatic patients, it is acceptable to "watch and wait" until the patient becomes symptomatic or the disease pace appears to be accelerating. Over time, the disease may transform to a more aggressive histology. The median survival is 8 to 10 years, and indolent patients often receive 3 or more treatments during the treatment phase of their disease. Initial treatment of the symptomatic indolent NHL patient historically has been combination chemotherapy. The most commonly used agents include: cyclophosphamide, vincristine and prednisone (CVP); or cyclophosphamide, adriamycin, vincristine, prednisone (CHOP). Approximately 70% to 80% of patients will respond to their initial chemotherapy, duration of remissions last on the order of 2-3 years. Ultimately the majority of patients relapse. The discovery and clinical use of the anti-CD20 antibody, rituximab, has provided significant improvements in response and survival rate. The current standard of care for most patients is rituximab+CHOP (R-CHOP) or rituximab+CVP (R-CVP). Interferon is approved for initial treatment of NHL in combination with alkylating agents, but has limited use in the U.S. Rituximab therapy has been shown to be efficacious in several types of NHL, and is currently approved as a first line treatment for both indolent (follicular lymphoma) and aggressive NHL (diffuse large B cell lymphoma). However, there are significant limitations of anti-CD20 monoclonal antibody (mAb), including primary resistance (50% response in relapsed indolent patients), acquired resistance (50% response rate upon re-treatment), rare complete response (2% complete response rate in relapsed population), and a continued pattern of relapse. Finally, many B cells do not express CD20, and thus many B-cell disorders are not treatable using anti-CD20 antibody therapy.

In addition to NHL there are several types of leukemias that result from disregulation of B cells. Chronic lymphocytic leukemia (also known as "chronic lymphoid leukemia" or "CLL"), is a type of adult leukemia caused by an abnormal accumulation of B lymphocytes. In CLL, the malignant lymphocytes may look normal and mature, but they are not able to cope effectively with infection. CLL is the most common form of leukemia in adults. Men are twice as likely to develop CLL as women. However, the key risk factor is age. Over 75% of new cases are diagnosed in patients over age 50. More than 10,000 cases are diagnosed every year and the mortality is almost 5,000 a year (American Cancer Society, 2006; and SEER Cancer Statistics Review). CLL is an incurable disease but progresses slowly in most cases. Many people with CLL lead normal and active lives for many years. Because of its slow onset, early-stage CLL is generally not treated since it is believed that early CLL intervention does not improve survival time or quality of life. Instead, the condition is monitored over time. Initial CLL treatments vary depending on the exact diagnosis and the progression of the disease. There are dozens of agents used for CLL therapy. Combination chemotherapy regimens such as FCR (fludarabine, cyclophosphamide and rituximab), and BR (Ibrutinib and rituximab) are effective in both newly-diagnosed and relapsed CLL. Allogeneic bone marrow (stem cell) transplantation is rarely used as a first-line treatment for CLL due to its risk.

Another type of leukemia is acute lymphoblastic leukemia (ALL), also known as acute lymphocytic leukemia. ALL is characterised by the overproduction and continuous multiplication of malignant and immature white blood cells (also known as lymphoblasts) in the bone marrow. 'Acute' refers to the undifferentiated, immature state of the circulating lymphocytes ("blasts"), and that the disease progresses rapidly with life expectancy of weeks to months if left untreated. ALL is most common in childhood with a peak incidence of 4-5 years of age. Children of age 12-16 die more easily from it than others. Currently, at least 80% of childhood ALL are considered curable. Under 4,000 cases are diagnosed every year and the mortality is almost 1,500 a year (American Cancer Society, 2006; and SEER Cancer Statistics Review).

The human CD 19 molecule is a structurally distinct cell surface receptor expressed on the surface of human B cells, including, but not limited to, pre-B cells, B cells in early development {i.e., immature B cells), mature B cells through terminal differentiation into plasma cells, and malignant B cells. CD 19 is expressed by most pre-B acute lymphoblastic leukemias (ALL), non-Hodgkin's lymphomas, B cell chronic lymphocytic leukemias (CLL), pro-lymphocytic leukemias, hairy cell leukemias, common acute lymphocytic leukemias, and some Null-acute lymphoblastic leukemias (Nadler et al, J. Immunol., 131:244-250 (1983), Loken et al, Blood, 70:1316-1324 (1987), Uckun et al, Blood, 71:13-29 (1988), Anderson et al, 1984. Blood, 63:1424-1433 (1984), Scheuermann, Leuk. Lymphoma, 18:385-397(1995)). The expression of CD 19 on plasma cells further suggests it may be expressed on differentiated B cell tumors such as multiple myeloma, plasmacytomas, Waldenstrom's tumors (Grossbard et al., Br. J. Haematol, 102:509-15(1998); Treon et al, Semin. Oncol, 30:248-52 (2003)).

Therefore, the CD 19 antigen is a target for immunotherapy in the treatment of non-Hodgkin's lymphoma (including each the subtypes described herein), chronic lymphocytic leukemia and/or acute lymphoblastic leukemia.

Certain CD19 therapies have been shown. T cells expressing an anti-CD19 chimeric antigen receptor (CAR) including both CD3-ζ, and the 4-BB costimulatory domain were administered to three patients with advanced CLL. Kalos et al., T cells with Chimeric Antigen Receptors Have Potent Antitumor Effects and Can Establish Memory in Patients with Advanced Leukemia, Science Translational Medicine, vol. 3, no. 95 (10 Aug. 2011), which is incorporated by reference in its entirety. Sadelain et al., The promise and potential pitfalls of chimeric antigen receptors, Current Opinion in Immunology, Elsevier, vol. 21, no. 2, 2 Apr. 2009, which is incorporated by reference in its entirety, also describes anti-CD19 chimeric antigen receptors (CARs). Neither Kalos et al. nor Sadelain et al., however, describe the antibody specific for CD19 in combination with a Bruton's tyrosine kinase (BTK) inhibitor as exemplified herein.

The use of a CD19 antibody in non-specific B cell lymphomas is discussed in WO2007076950 (US2007154473), which are both incorporated by reference in their entireties, along with the cursory mention of Ibrutinib within a long list of potential combination partners, but fails either to teach the antibody exemplified herein or suggest the synergistic effects of the combination in the treatment of non-Hodgkin's lymphoma, chronic lymphocytic leukemia and/or acute lymphoblastic leukemia as exemplified herein.

The use of a CD19 antibody in CLL, NHL and ALL is described in Scheuermann et al., CD19 Antigen in Leukemia and Lymphoma Diagnosis and Immunotherapy, Leukemia and Lymphoma, Vol. 18, 385-397 (1995), which is incorporated by reference in its entirety, but fails to suggest the combination exemplified herein.

Additional antibodies specific for CD19 are described in WO2005012493 (U.S. Pat. No. 7,109,304), WO2010053716 (U.S. Ser. No. 12/266,999) (Immunomedics); WO2007002223 (US U.S. Pat. No. 8,097,703) (Medarex); WO2008022152 (Ser. No. 12/377,251) and WO2008150494 (Xencor), WO2008031056 (U.S. Ser. No. 11/852,106) (Medimmune); WO 2007076950 (U.S. Ser. No. 11/648,505) (Merck patent GmbH); WO 2009/052431 (U.S. Ser. No. 12/253,895) (Seattle Genetics); and WO2010095031 (Ser. No. 12/710,442) (Glenmark Pharmaceuticals), WO2012010562 and WO2012010561 (International Drug Development), WO2011147834 (Roche Glycart), and WO 2012/156455 (Sanofi), which are all incorporated by reference in their entireties.

Combinations of antibodies specific for CD19 and other agents are described in WO2010151341 (U.S. Ser. No. 13/377,514) (The Feinstein Institute); U.S. Pat. No. 5,686,072 (University of Texas), and WO2002022212 (PCT/US01/29026) (IDEC Pharmaceuticals), WO2013/024097 (Ser. No. 14/126,928) (MorphoSys AG) and WO2013/024095 (Ser. No. 14/127,217) (MorphoSys AG), which are all incorporated by reference in their entireties.

Certain bruton's tyrosine kinase inhibitors are commercially available. Ibrutinib, also known as PCI-32765, and marketed under the name Imbruvica is an anticancer drug targeting B-cell malignancies. Ibrutinib is described in U.S. Pat. Nos. 7,514,444; 8,008,309; 8,697,711; 8,735,403; 8,957,079; and 8,754,090, which are all incorporated by reference in their entireties.

Ibrutinib has been tested in combination with rituximab (an anti-CD20 antibody). Burger et al., Lancet Oncol., 2014 September, 15(19): 1090-1099. Ibrutinib potentially inhibits the ADCC activity of certain CD20 antibodies in vitro. Duong et al., mAbs, January/February 2015, 192-198, and Kohrt et al., Blood, 2014, 123:1957-1960.

It is clear that in spite of the recent progress in the discovery and development of anticancer agents, many forms of cancer involving CD19-expressing tumors still have a poor prognosis. Thus, there is a need for improved methods for treating such forms of cancer.

SUMMARY

Neither alone nor in combination does the prior art suggest the synergistic effects of the combination of the exemplified antibody and Ibrutinib in the treatment of non-Hodgkin's lymphoma, chronic lymphocytic leukemia and/or acute lymphoblastic leukemia.

In one aspect, the present disclosure relates to a synergistic combination of an antibody specific for CD19 and a Bruton's tyrosine kinase (BTK) inhibitor. Such combinations are useful in the treatment of B cell malignancies, such as, non-Hodgkin's lymphoma, chronic lymphocytic leukemia and/or acute lymphoblastic leukemia.

In vitro models are considered indicative of how a certain compound or combination of compounds would behave in humans.

MEC-1 cells in this in vitro model are indicative of how the combination will work in the treatment of chronic lymphoid leukemia (CLL) in humans. Ramos cells in this in vitro model are indicative of how the combination will work in the treatment of non-Hogkins lymphoma (NHL) in humans. MEC-1 cells (DSMZ # ACC497) are a chronic B-cell leukemia cell line. Ramos cells (ATCC number CRL-1596), a human Burkitt's lymphoma cells.

In addition, when compounds are combined in vitro, one expects that the combination has only additive effects. Surprisingly, the inventors found that the combination of a particular antibody specific for CD19 and Ibrutinib mediated a synergistic level of specific cell killing in vitro in comparison to the antibody and Ibrutinib alone. Specifically, the inventors found that the combination of MOR00208 and Ibrutinib mediated a synergistic level of specific cell killing in vitro in MEC-1 cells compared to the antibody and Ibrutinib alone.

In addition, and also unexpectedly, the inventors found that the combination of a particular antibody specific for CD19 and Ibrutinib had certain functional properties, in comparison to the antibody and Ibrutinib alone.

In summary, the combination of the exemplified anti-CD19 antibody and Ibrutinib behaved synergistically in models relevant to CLL. As CLL is a B cell related disorders and CD19 is highly expressed on B-cells, the exemplified combination would have the same mechanism of action and should also behave synergistically in the treatment of other B cell related disorders, e.g. ALL and NHL.

Therefore, the combination of the exemplified antibody specific for CD19 and Ibrutinib should be effective in the treatment of humans in non-Hodgkin's lymphoma, chronic lymphocytic leukemia and/or acute lymphoblastic leukemia. The expected efficacy of the combination of the antibody specific to CD19 exemplified and Ibrutinib will be confirmed in clinical trials.

As the mechanism of action of Ibrutinib and other Bruton's tyrosine kinase (BTK) inhibitors are similar, as they all work by inhibiting the tyrosine-protein kinase BTK enzyme, which plays a crucial role in B-cell development, it is believed that synergy should also be seen when treating humans having non-Hodgkin's lymphoma, chronic lymphocytic leukemia and/or acute lymphoblastic leukemia with a combination of the exemplified anti-CD19 antibody and a Bruton's tyrosine kinase (BTK) inhibitor other than Ibrutinib.

As the exemplified anti-CD19 antibody and other anti-CD19 antibodies bind CD19, it is believed that synergy should also be seen when treating humans having non-Hodgkin's lymphoma, chronic lymphocytic leukemia and/or acute lymphoblastic leukemia with a combination of any anti-CD19 antibody and a Bruton's tyrosine kinase (BTK) inhibitor, e.g., Ibrutinib.

An aspect of the present disclosure comprises a synergistic combination wherein the antibody specific for CD19 comprises an HCDR1 region of sequence SYVMH (SEQ ID NO: 1), an HCDR2 region of sequence NPYNDG (SEQ ID NO: 2), an HCDR3 region of sequence GTYYYGTRVFDY (SEQ ID NO: 3), an LCDR1 region of sequence RSSKSLQNVNGNTYLY (SEQ ID NO: 4), an LCDR2 region of sequence RMSNLNS (SEQ ID NO: 5), and an LCDR3 region of sequence MQHLEYPIT (SEQ ID NO: 6) and Ibrutinib. In preferred aspects, the combination is used for the treatment of non-Hodgkin's lymphoma, chronic lymphocytic leukemia and/or acute lymphoblastic leukemia.

DESCRIPTION OF DRAWINGS

FIG. 4 shows the amino acid sequence of the variable domains of MOR00208.

FIG. 5 shows the amino acid sequence of the Fc regions of MOR00208.

DETAILED DESCRIPTION OF THE INVENTION

Figure 1:
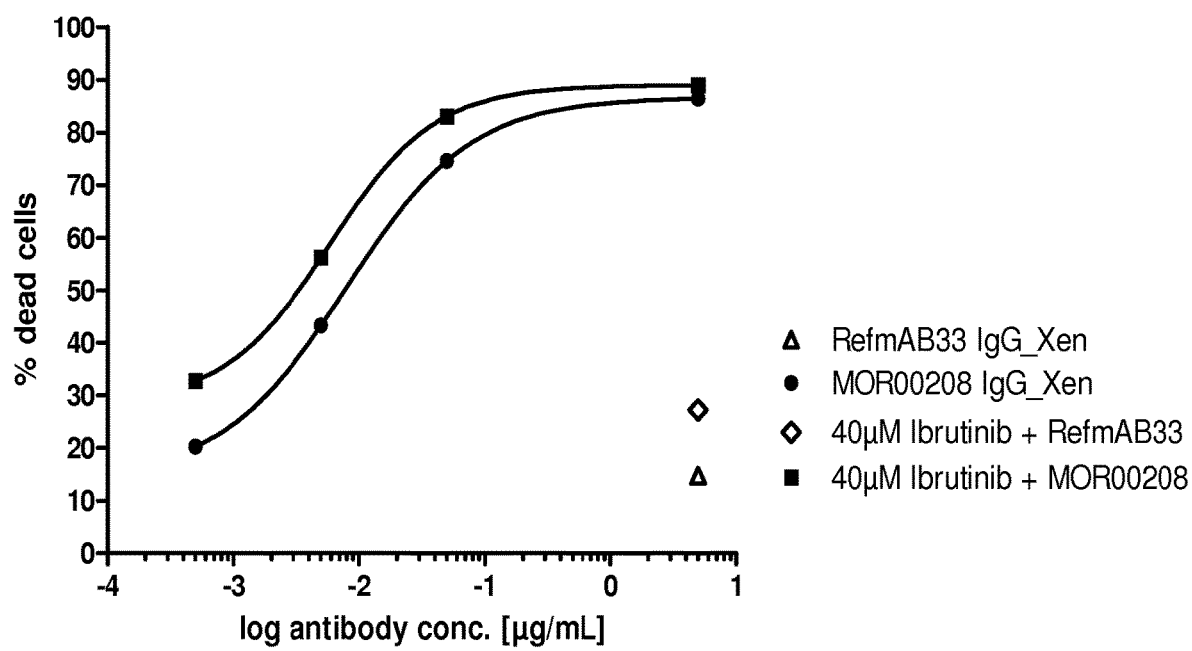
FIG. 1 shows the cytotoxicity effects of MOR00208 and Ibrutinib alone and in combination on Ramos cells. Ramos cells were pre-treated with 40 µM Ibrutinib for 24 hours.

"Synergy", "synergism" or "synergistic" mean more than the expected additive effect of a combination. The "synergy", "synergism" or "synergistic" effect of a combination is determined herein by the methods of Chou et al., Clarke et al. and/or Webb et al. See Ting-Chao Chou, Theoretical Basis, Experimental Design, and Computerized Simulation of Synergism and Antagonism in Drug Combination Studies, Pharmacol Rev 58:621-681 (2006), which is incorporated by reference in its entirety. See also Clarke et al., Issues in experimental design and endpoint analysis in the study of experimental cytotoxic agents in vivo in breast cancer and other models, Breast Cancer Research and Treatment 46:255-278 (1997), which is incorporated by reference in its entirety. See also Webb, J. L. (1963) Enzyme and Metabolic Inhibitors, Academic Press, New York, which is incorporated by reference in its entirety.

The term "antibody" means monoclonal antibodies, including any isotype, such as, IgG, IgM, IgA, IgD and IgE. An IgG antibody is comprised of two identical heavy chains and two identical light chains that are joined by disulfide bonds. Each heavy and light chain contains a constant region and a variable region. Each variable region contains three segments called "complementarity-determining regions" ("CDRs") or "hypervariable regions", which are primarily responsible for binding an epitope of an antigen. They are referred to as CDR1, CDR2, and CDR3, numbered sequentially from the N-terminus. The more highly conserved portions of the variable regions outside of the CDRs are called the "framework regions". An "antibody fragment" means an Fv, scFv, dsFv, Fab, Fab' F(ab')2 fragment, or other fragment, which contains at least one variable heavy or variable light chain, each containing CDRs and framework regions.

A "Bruton's tyrosine kinase (BTK) inhibitor" is a class of drug that functions by inhibiting the tyrosine-protein kinase BTK enzyme, which plays an important role in B-cell development. Specifically, BTK contains a PH domain that binds phosphatidylinositol (3,4,5)-trisphosphate (PIP3). PIP3 binding induces Btk to phosphorylate phospholipase C, which in turn hydrolyzes PIP2, a phosphatidylinositol, into two second messengers, inositol triphosphate (IP3) and diacylglycerol (DAG), which then go on to modulate the activity of downstream proteins during B-cell signalling.

Bruton's tyrosine kinase (BTK) inhibitors include Ibrutinib. Ibrutinib is marketed by Pharmacyclics, Inc and Johnson & Johnson's Janssen Pharmaceutical (trade name Imbruvica, also named PCI-32765). Ibrutinib is currently labelled for the treatment of patients with Mantle cell lymphoma (MCL) who have received at least one prior therapy, Chronic lymphocytic leukemia (CLL) who have received at least one prior therapy, Chronic lymphocytic leukemia with 17p deletion, and Waldenström's macroglobulinemia. The formula of Ibrutinib is 1-[(3R)-3-[4-amino-3-(4-phenoxyphenyl)-1H-pyrazolo[3,4-d]pyrimidin-1-yl]-1-piperidinyl]-2-propen-1-one and has the following structure:

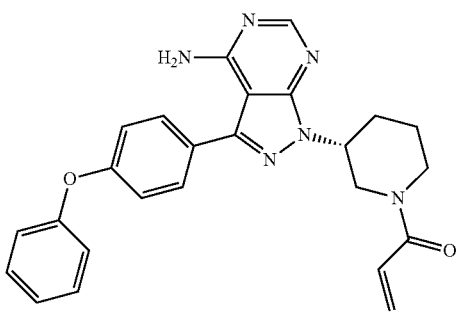 [SMILES: C=CC(=O)N1CCC[C@@H](n2nc(-c3ccc(Oc4ccccc4)cc3)c3c(N)ncnc32)C1]

Ibrutinib is a small-molecule inhibitor of BTK. Ibrutinib forms a covalent bond with a cysteine residue in the BTK active site, leading to inhibition of BTK enzymatic activity. BTK is a signaling molecule of the B-cell antigen receptor (BCR) and cytokine receptor pathways. BTK's role in signaling through the B-cell surface receptors results in activation of pathways necessary for B-cell trafficking, chemotaxis, and adhesion. Nonclinical studies show that ibrutinib inhibits malignant B-cell proliferation and survival in vivo as well as cell migration and substrate adhesion in vitro.

Additional Bruton's tyrosine kinase (BTK) inhibitors include:

ACP-196 (Acerta Pharma BV), which is described in WO 2012170976 (U.S. application Ser. No. 14/112,428), WO 2013010380 (U.S. application Ser. No. 14/233,478), and WO 2014113932 (U.S. application Ser. No. 14/160,587), which are all incorporated by reference in their entireties;

BGB-3111 (BeiGene, Co., Ltd.), and CC-292 Evans et al. 2013

"VH" refers to the variable region of an immunoglobulin heavy chain of an antibody, or antibody fragment. "VL" refers to the variable region of the immunoglobulin light chain of an antibody, or antibody fragment.

The term "CD19" refers to the protein known as CD19, having the following synonyms: B4, B-lymphocyte antigen CD19, B-lymphocyte surface antigen B4, CVID3, Differentiation antigen CD19, MGC12802, and T-cell surface antigen Leu-12.

Human CD19 has the amino acid sequence of:

(SEQ ID NO: 7)
MPPPRLLFFLLFLTPMEVRPEEPLVVKVEEGDNAVLQCLKGTSDGPTQQL

TWSRESPLKPFLKLSLGLPGLGIHMRPLAIWLFIFNVSQQMGGFYLCQPG

PPSEKAWQPGWTVNVEGSGELFRWNVSDLGGLGCGLKNRSSEGPSSPSGK

LMSPKLYVWAKDRPEIWEGEPPCLPPRDSLNQSLSQDLTMAPGSTLWLSC

GVPPDSVSRGPLSWTHVHPKGPKSLLSLELKDDRPARDMWVMETGLLLPR

ATAQDAGKYYCHRGNLTMSFHLEITARPVLWHWLLRTGGWKVSAVTLAYL

IFCLCSLVGILHLQRALVLRRKRKRMTDPIRRFFKVIPPPGSGPQNQYGN

VLSLPTPTSGLGRAQRWAAGLGGTAPSYGNPSSDVQADGALGSRSPPGVG

PEEEEGEGYEEPDSEEDSEFYENDSNLGQDQLSQDGSGYENPEDEPLGPE

DEDSFSNAESYENEDEELTQPVARTMDFLSPHGSAWDPSREATSLGSQSY

EDMRGILYAAPQLRSIRGQPGPNHEEDADSYENMDNPDGPDPAWGGGGRM

GTWSTR.

"MOR00208" is an anti-CD19 antibody. The amino acid sequence of the variable domains is provided in FIG. 4. The amino acid sequence of the heavy and light chain Fc regions of MOR00208 are provided in FIG. 5. "MOR00208" and "XmAb 5574" are used as synonyms to describe the antibody shown in FIGS. 4 and 5. The MOR00208 antibody is described in U.S. patent application Ser. No. 12/377,251, which is incorporated by reference in its entirety.

U.S. patent application Ser. No. 12/377,251 describes the antibody named 4G7 H1.52 Hybrid S239D/I332E/4G7 L1.155 (later named MOR00208) as follows:

>4G7 H1.52 Hybrid S239D/I332E
(SEQ ID NO: 14)
EVQLVESGGGLVKPGGSLKLSCAASGYTFTSYVMHWVRQAPGKGLEWIGY

INPYNDGTKYNEKFQGRVTISSDKSISTAYMELSSLRSEDTAMYYCARGT

YYYGTRVFDYWGQGTLVTVSSASTKGPSVFPLAPSSKSTSGGTAALGCLV

KDYFPEPVTVSWNSGALTSGVHTFPAVLQSSGLYSLSSVVTVPSSSLGTQ

TYICNVNHKPSNTKVDKKVEPKSCDKTHTCPPCPAPELLGGPDVFLFPPK

PKDTLMISRTPEVTCVVVDVSHEDPEVQFNWYVDGVEVHNAKTKPREEQF

NSTFRVVSVLTVVHQDWLNGKEYKCKVSNKALPAPEEKTISKTKGQPREP

QVYTLPPSREEMTKNQVSLTCLVKGFYPSDIAVEWESNGQPENNYKTIPP

MLDSDGSFFLYSKLTVDKSRWQQGNVFSCSVMHEALHNHYTQKSLSLSPG

K

>4G7 L1.155
(SEQ ID NO: 15)
DIVMTQSPATLSLSPGERATLSCRSSKSLQNVNGNTYLYWFQQKPGQSPQ

LLIYRMSNLNSGVPDRFSGSGSGTEFTLTISSLEPEDFAVYYCMQHLEYP

ITFGAGTKLEIKRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGEC

Additional antibodies specific for CD19 are described in U.S. Pat. No. 7,109,304 (Immunomedics), which is incorporated by reference in its entirety; U.S. application Ser. No. 11/917,750 (Medarex), which is incorporated by reference in its entirety; U.S. application Ser. No. 11/852,106 (Medimmune), which is incorporated by reference in its entirety; U.S. application Ser. No. 11/648,505 (Merck patent GmbH), which is incorporated by reference in its entirety; U.S. Pat. No. 7,968,687 (Seattle Genetics), which is incorporated by reference in its entirety; and U.S. application Ser. No. 12/710,442 (Glenmark Pharmaceuticals), which is incorporated by reference in its entirety.

"Fc region" means the constant region of an antibody, which in humans may be of the IgG1, 2, 3, 4 subclass or others. The sequences of human Fc regions are available at IMGT, Human IGH C-REGIONs, http://www.imgt.org/IMGTrepertoire/Proteins/protein/human/IGH/IGHC/Hu_IGH-Callgenes.html (retrieved on 16 May 2011).

"RefmAb33" is an antibody whose amino acid sequence is as follows:

Heavy chain including the Fc region:
(SEQ ID NO: 8)
QVTLRESGPALVKPTQTLTLTCTFSGFSLSTAGMSVGWIRQPPGKALEWL

ADIWWDDKKHYNPSLKDRLTISKDTSKNQVVLKVTNMDPADTATYYCARD

-continued

```
MIFNFYFDVWGQGTTVTVSSASTKGPSVFPLAPSSKSTSGGTAALGCLVK

DYFPEPVTVSWNSGALTSGVHTFPAVLQSSGLYSLSSVVTVPSSSLGTQT

YICNVNHKPSNTKVDKKVEPKSCDKTHTCPPCPAPELLGGPDVFLFPPKP

KDTLMISRTPEVICVVVDVSHEDPEVQFNWYVDGVEVHNAKTKPREEQFN

STFRVVSVLIVVHQDWLNGKEYKCKVSNKALPAPEEKTISKTKGQPREPQ

VYTLPPSREEMTKNQVSLTCLVKGFYPSDIAVEWESNGQPENNYKTTPPM

LDSDGSFFLYSKLTVDKSRWQQGNVFSCSVMHEALHNHYTQKSLSLSPGK

Light chain including the Fc region:
                                       (SEQ ID NO: 9)
DIQMTQSPSTLSASVGDRVTITCSASSRVGYMHWYQQKPGKAPKLLIYDT

SKLASGVPSRFSGSGSGTEFTLTISSLQPDDFATYYCFQGSGYPFTFGGG

TKVEIKRTVAAPSVFIFPPSDEQLKSGTASVVCLLNNFYPREAKVQWKVD

NALQSGNSQESVTEQDSKDSTYSLSSTLTLSKADYEKHKVYACEVTHQGL

SSPVTKSFNRGEC
```

RefmAb33 is specific for RSV, and is used as isotype control, as it shares the same Fc region as MOR00208.

A "combination" means more than one item, e.g. a compound such as an antibody and Ibrutinib.

The present disclosure also relates to combinations, pharmaceuticals, and pharmaceutical compositions containing the described combinations. The two components of the synergistic combination of the present invention, e.g. the antibody specific for CD19 and Ibrutinib, may be administered together, simultaneously, separately or subsequently, either physically or in time.

Ibrutinib is currently taken orally and is currently dosed once per day. MOR00208 is currently administered intravenously, and is currently dosed either once a week or once every two weeks.

Preferably, administration of both drugs allows for both drugs to be active in the patent at the same time. For example, if MOR208 is dosed weekly and Ibritinib is dosed daily then the active substance of both drugs is present in the patient at the same time. In an embodiment, Ibrutinib, is administered prior to and/or separately from the administration of the antibody specific for CD19, e.g. MOR00208.

Simultaneously means that the two components are administered at a time where both components (drugs) are active in the patient at the same time. It is implied by "synergism" that both drugs are active in the patient at the same time.

Administered together can mean administered at the same time.

The two components may be formulated in different pharmaceutical compositions. A pharmaceutical composition includes an active agent, eg. an antibody for therapeutic use in humans. A pharmaceutical composition may include acceptable carriers or excipients.

"Administered" or "administration" includes but is not limited to delivery by an injectable form, such as, for example, an intravenous, intramuscular, intradermal or subcutaneous route or mucosal route, for example, as a nasal spray or aerosol for inhalation or as an ingestable solution, capsule or tablet.

A "therapeutically effective amount" of a compound or combination refers to an amount sufficient to cure, alleviate or partially arrest the clinical manifestations of a given disease or disorder and its complications. The amount that is effective for a particular therapeutic purpose will depend on the severity of the disease or injury as well as on the weight and general state of the subject. It will be understood that determination of an appropriate dosage may be achieved, using routine experimentation, by constructing a matrix of values and testing different points in the matrix, all of which is within the ordinary skills of a trained physician or clinical scientist.

The "CDRs" herein are defined by either Chothia et al or Kabat et al. See Chothia C, Lesk A M. (1987) Canonical structures for the hypervariable regions of immunoglobulins. J Mol Biol., 196(4):901-17, which is incorporated by reference in its entirety. See Kabat E. A, Wu T. T., Perry H. M., Gottesman K. S. and Foeller C. (1991). Sequences of Proteins of Immunological Interest. 5th edit., NIH Publication no. 91-3242, US Dept. of Health and Human Services, Washington, D.C., which is incorporated by reference in its entirety.

"Cross competes" means the ability of an antibody or other binding agent to interfere with the binding of other antibodies or binding agents to CD19 in a standard competitive binding assay. The ability or extent to which an antibody or other binding agent is able to interfere with the binding of another antibody or binding molecule to CD19, and, therefore whether it can be said to cross-compete according to the invention, can be determined using standard competition binding assays. One suitable assay involves the use of the Biacore technology (e.g. by using the BIAcore 3000 instrument (Biacore, Uppsala, Sweden)), which can measure the extent of interactions using surface plasmon resonance technology. Another assay for measuring cross-competing uses an ELISA-based approach. A high throughput process for "epitope binning" antibodies based upon their cross-competition is described in International Patent Application No. WO 2003/48731

The term "epitope" includes any protein determinant capable of specific binding to an antibody or otherwise interacting with a molecule. Epitopic determinants generally consist of chemically active surface groupings of molecules such as amino acids or carbohydrate or sugar side chains and can have specific three-dimensional structural characteristics, as well as specific charge characteristics. An epitope may be "linear" or "conformational." The term "linear epitope" refers to an epitope with all of the points of interaction between the protein and the interacting molecule (such as an antibody) occur linearly along the primary amino acid sequence of the protein (continuous). The term "conformational epitope" refers to an epitope in which discontinuous amino acids that come together in three dimensional conformation. In a conformational epitope, the points of interaction occur across amino acid residues on the protein that are separated from one another.

"Binds the same epitope as" means the ability of an antibody or other binding agent to bind to CD19 and having the same epitope as the exemplified antibody. The epitopes of the exemplified antibody and other antibodies to CD19 can be determined using standard epitope mapping techniques. Epitope mapping techniques, well known in the art. include Epitope Mapping Protocols in Methods in Molecular Biology, Vol. 66 (Glenn E. Morris, Ed., 1996) Humana Press, Totowa, N.J. For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al, (1984) Proc.

Natl. Acad. Sci. USA 8:3998-4002; Geysen et al, (1985) Proc. Natl. Acad. Sci. USA 82:78-182; Geysen et al, (1986) Mol. Immunol. 23:709-715. Similarly, conformational epitopes are readily identified by determining spatial conformation of amino acids such as by, e.g., hydrogen/deuterium exchange, x-ray crystallography and two-dimensional nuclear magnetic resonance. See, e.g., Epitope Mapping Protocols, supra. Antigenic regions of proteins can also be identified using standard antigenicity and hydropathy plots, such as those calculated using, e.g., the Omiga version 1.0 software program available from the Oxford Molecular Group. This computer program employs the Hopp/Woods method, Hopp et al, (1981) Proc. Natl. Acad. Sci USA 78:3824-3828; for determining antigenicity profiles, and the Kyte-Doolittle technique, Kyte et al, (1982) J. Mol. Biol. 157: 105-132; for hydropathy plots.

Embodiments

An aspect of the present disclosure is a combination comprising an antibody specific for CD19 and a Bruton's tyrosine kinase (BTK) inhibitor for use in the treatment of non-Hodgkin's lymphoma, chronic lymphocytic leukemia and/or acute lymphoblastic leukemia. In embodiments, the combination is synergistic.

Herein, the combination of the exemplified anti-CD19 antibody and Ibrutinib behaved synergistically in in vitro models relevant to CLL. As CLL is a B cell related disorder and CD19 is highly expressed on B-cells, the exemplified combination should have the same mechanism of action and should also behave synergistically in the treatment of other B cell related disorders, e.g. ALL and NHL. Therefore, the combination of the exemplified antibody specific for CD19 and Ibrutinib should be effective in the treatment of humans in non-Hodgkin's lymphoma, chronic lymphocytic leukemia and/or acute lymphoblastic leukemia. The expected efficacy of the combination of the antibody specific to CD19 exemplified and Ibrutinib will be confirmed in clinical trials.

MEC-1 cells (DSMZ # ACC497) a chronic B-cell leukemia cell line was tested. MEC-1 cells in this in vitro model are indicative of how the combination will work in the treatment of chronic lymphoid leukemia (CLL) in humans. The Chou index values indicate clear synergism of the combination of MOR00208 and Ibrutinib in the specific killing of MEC-1 cells as compared to MOR00208 and Ibrutinib alone.

Additional cell lines are evaluated: Ramos cells (ATCC number CRL-1596), a human Burkitt's lymphoma cells. HG-3 (DSMZ # ACC765), and CII (DSMZ # ACC773) are a chronic lymphocytic leukemia cell line. Su-DHL 6 (DSMZ # ACC572), U2932 (DSMZ # ACC633) and OCI-LY7 (DSMZ # ACC688) are a Diffuse large B-cell lymphoma (DLBCL) cell line. JVM-2 (ATCC® CRL-3002) is a mantle cell lymphoma cell line. BALL-1 (DSMZ # ACC742) is an acute lymphoblastic leukemia cell line.

Ramos cells in this in vitro model are indicative of how the combination will work in the treatment of non-Hogkins lymphoma (NHL) in humans. HG-3 and CII cells in this in vitro model are indicative of how the combination will work in the treatment of chronic lymphoid leukemia (CLL) in humans. Su-DHL 6, U2932 and OCI-LY7 cells in this in vitro model are indicative of how the combination will work in the treatment non-Hodgkin's lymphoma in humans. JVM-2 cells in this in vitro model are indicative of how the combination will work in the treatment non-Hodgkin's lymphoma in humans. BALL-1 cells in this in vitro model are indicative of how the combination will work in the treatment of acute lymphoblastic leukemia in humans.

In summary, the combination of the exemplified anti-CD19 antibody and Ibrutinib behaved synergistically in models relevant to CLL.

Therefore, the combination of the exemplified antibody specific for CD19 and Ibrutinib should be effective in the treatment of humans in non-Hodgkin's lymphoma, chronic lymphocytic leukemia and/or acute lymphoblastic leukemia.

As the mechanism of action of Ibrutinib and other Bruton's tyrosine kinase (BTK) inhibitors are similar, as they all work by inhibiting the tyrosine-protein kinase BTK enzyme, which plays a crucial role in B-cell development, it is believed that synergy should also be seen when treating humans having non-Hodgkin's lymphoma, chronic lymphocytic leukemia and/or acute lymphoblastic leukemia with a combination of the exemplified anti-CD19 antibody and a Bruton's tyrosine kinase (BTK) inhibitor other than Ibrutinib.

As the exemplified anti-CD19 antibody and other anti-CD19 antibodies bind CD19, it is believed that synergy should also be seen when treating humans having non-Hodgkin's lymphoma, chronic lymphocytic leukemia and/or acute lymphoblastic leukemia with a combination of any anti-CD19 antibody and a Bruton's tyrosine kinase (BTK) inhibitor, where the anti-CD19 antibody is, for example, described in U.S. patent application Ser. No. 12/377,251 (Xencor), WO2005012493, WO2010053716 (Immunomedics); WO2007002223 (Medarex); WO2008022152 (Xencor); WO2008031056 (Medimmune); WO 2007/076950 (Merck patent GmbH); WO 2009/052431 (Seattle Genetics); and WO2010095031 (Glenmark Pharmaceuticals), all of which are incorporated by reference in their entireties.

In embodiments, the antibody specific for CD19 comprises an antibody that cross-competes with the antibody comprising an HCDR1 region of sequence SYVMH (SEQ ID NO: 1), an HCDR2 region of sequence NPYNDG (SEQ ID NO: 2), an HCDR3 region of sequence GTYYYG-TRVFDY (SEQ ID NO: 3), an LCDR1 region of sequence RSSKSLQNVNGNTYLY (SEQ ID NO: 4), an LCDR2 region of sequence RMSNLNS (SEQ ID NO: 5), and an LCDR3 region of sequence MQHLEYPIT (SEQ ID NO: 6).

In embodiments, the antibody specific for CD19 comprises an antibody that binds to the same epitope as an antibody comprising an HCDR1 region of sequence SYVMH (SEQ ID NO: 1), an HCDR2 region of sequence NPYNDG (SEQ ID NO: 2), an HCDR3 region of sequence GTYYYGTRVFDY (SEQ ID NO: 3), an LCDR1 region of sequence RSSKSLQNVNGNTYLY (SEQ ID NO: 4), an LCDR2 region of sequence RMSNLNS (SEQ ID NO: 5), and an LCDR3 region of sequence MQHLEYPIT (SEQ ID NO: 6).

In embodiments, the antibody specific for CD19 comprises an HCDR1 region of sequence SYVMH (SEQ ID NO: 1), an HCDR2 region of sequence NPYNDG (SEQ ID NO: 2), an HCDR3 region of sequence GTYYYGTRVFDY (SEQ ID NO: 3), an LCDR1 region of sequence RSSKSLQNVNGNTYLY (SEQ ID NO: 4), an LCDR2 region of sequence RMSNLNS (SEQ ID NO: 5), and an LCDR3 region of sequence MQHLEYPIT (SEQ ID NO: 6).

In embodiments, the antibody specific for CD19 comprises a variable heavy chain of the sequence EVQLVES-GGGLVKPGGSLKLSCAASGYTFTSYVMH-WVRQAPGKGLEWIGYINPY NDGTKYNEKFQGRVTISSDKSISTAYMELSSLRSED-TAMYYCARGTYYYGTRVFDYWG QGTLVTVSS (SEQ ID NO: 10) and a variable light chain of the sequence DIVMTQSPATLSLSPGERATLSCRSSKSLQNVNGNTY-
LYWFQQKPGQSPQLLIYR MSNLNSGVPDRFSGSGS-
GTEFTLTISSLEPEDFAVYYCMQHLEYPITFGAGT-
KLEIK (SEQ ID NO: 11).

In certain embodiments said antibody comprises a heavy chain constant domain of the sequence (SEQ ID NO: 12)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPDVFLFPPKPKDTLMISRTPEVTCVVVDVS

HEDPEVQFNWYVDGVEVHNAKTKPREEQFNSTFRVVSVLTVVHQDWLNGK

EYKCKVSNKALPAPEEKTISKTKGQPREPQVYTLPPSREEMTKNQVSLTC

LVKGFYPSDIAVEWESNGQPENNYKTTPPMLDSDGSFFLYSKLTVDKSRW

QQGNVFSCSVMHEALHNHYTQKSLSLSPGK.

In embodiments, the antibody specific for CD19 comprises a light chain constant domain of the sequence (SEQ ID NO: 13)
RTVAAPSVFIFPPSDEQLKSGTASVVCLLNNFYPREAKVQWKVDNALQSG

NSQESVTEQDSKDSTYSLSSTLTLSKADYEKHKVYACEVTHQGLSSPVTK

SFNRGEC.

In embodiments, the Bruton's tyrosine kinase (BTK) inhibitor is Ibrutinib.

In embodiments, the components of the combination, the antibody specific for CD19 and Ibrutinib, are administered separately. In an embodiment, Ibrutinib is administered prior to administration of the antibody specific for CD19.

In embodiments, the components of the combination are administered at a time where both components (drugs) are active in the patient at the same time. It is implied by "synergism" that both drugs are active in the patient at the same time. In embodiments, the components of the combination are administered together, simultaneously, separately or subsequently, either physically or in time. In embodiments, the components of the combination are administered simultaneously.

In embodiments the combination is a pharmaceutical composition. In embodiments, the composition comprises an acceptable carrier. In embodiments, the combination is administered in an effective amount.

In another aspect the synergistic combination of an antibody specific for CD19 comprising an HCDR1 region of sequence SYVMH (SEQ ID NO: 1), an HCDR2 region of sequence NPYNDG (SEQ ID NO: 2), an HCDR3 region of sequence GTYYYGTRVFDY (SEQ ID NO: 3), an LCDR1 region of sequence RSSKSLQNVNGNTYLY (SEQ ID NO: 4), an LCDR2 region of sequence RMSNLNS (SEQ ID NO: 5), and an LCDR3 region of sequence MQHLEYPIT (SEQ ID NO: 6) and Ibrutinib is able to mediate killing of MEC-1 cells by ADCC in the presence of isolated human PBMCs with an at least two-fold, three-fold, four-fold, or five-fold better efficacy than Ibrutinib alone.

An aspect of the present disclosure comprises a synergistic combination of an antibody specific for CD19 comprising an HCDR1 region of sequence SYVMH (SEQ ID NO: 1), an HCDR2 region of sequence NPYNDG (SEQ ID NO: 2), an HCDR3 region of sequence GTYYYGTRVFDY (SEQ ID NO: 3), an LCDR1 region of sequence RSSKSLQNVNGN-TYLY (SEQ ID NO: 4), an LCDR2 region of sequence RMSNLNS (SEQ ID NO: 5), and an LCDR3 region of sequence MQHLEYPIT (SEQ ID NO: 6) and Ibrutinib for the treatment of non-Hodgkin's lymphoma, chronic lymphocytic leukemia and/or acute lymphoblastic leukemia. In embodiments, the non-Hodgkin's lymphoma is selected from the group consisting of follicular lymphoma, small lymphocytic lymphoma, mucosa-associated lymphoid tissue, marginal zone, diffuse large B cell, Burkitt's, and mantle cell.

In embodiments, the non-Hodgkin's lymphoma is follicular lymphoma. In embodiments, the non-Hodgkin's lymphoma is small lymphocytic lymphoma. In embodiments, the non-Hodgkin's lymphoma is mucosa-associated lymphoid tissue. In embodiments, the non-Hodgkin's lymphoma is marginal zone lymphoma. In embodiments, the non-Hodgkin's lymphoma is diffuse large B cell lymphoma. In embodiments, the non-Hodgkin's lymphoma is Burkitt's lymphoma. In embodiments, the non-Hodgkin's lymphoma is mantle cell lymphoma.

In embodiments, the combination is for the treatment of chronic lymphocytic leukemia. In embodiments, the combination is for the treatment of acute lymphoblastic leukemia.

Another aspect comprises a method of treating non-Hodgkin's lymphoma, chronic lymphocytic leukemia and/or acute lymphoblastic leukemia in an individual in need thereof, which method comprises administration of an antibody specific for CD19 and a Bruton's tyrosine kinase (BTK) inhibitor. In embodiments of the method, the antibody specific for CD19 comprises an HCDR1 region of sequence SYVMH (SEQ ID NO: 1), an HCDR2 region of sequence NPYNDG (SEQ ID NO: 2), an HCDR3 region of sequence GTYYYGTRVFDY (SEQ ID NO: 3), an LCDR1 region of sequence RSSKSLQNVNGNTYLY (SEQ ID NO: 4), an LCDR2 region of sequence RMSNLNS (SEQ ID NO: 5), and an LCDR3 region of sequence MQHLEYPIT (SEQ ID NO: 6). In embodiments of the method, the antibody comprises the exemplified antibody specific for CD19. In embodiments of the method the Bruton's tyrosine kinase (BTK) inhibitor is Ibrutinib.

Another aspect includes a use of an antibody specific for CD19 wherein said antibody comprises an HCDR1 region of sequence SYVMH (SEQ ID NO: 1), an HCDR2 region of sequence NPYNDG (SEQ ID NO: 2), an HCDR3 region of sequence GTYYYGTRVFDY (SEQ ID NO: 3), an LCDR1 region of sequence RSSKSLQNVNGNTYLY (SEQ ID NO: 4), an LCDR2 region of sequence RMSNLNS (SEQ ID NO: 5), and an LCDR3 region of sequence MQHLEYPIT (SEQ ID NO: 6) in the manufacture of a medicament for the treatment of non-Hodgkin's lymphoma, chronic lymphocytic leukemia and/or acute lymphoblastic leukemia in synergistic combination with Ibrutinib.

EXAMPLES

Example 1: Cytotoxicity of MEC-1 Cells Using MOR00208 and Ibrutinib Alone and in Combination Materials Cell lines tested: MEC-1 cells (DSMZ # ACC497). Cell lines are tested: chronic B-cell leukemia cell line; JVM-2 (ATCC® CRL-3002) a mantle cell lymphoma cell line; Ramos cells (ATCC number CRL-1596), a human Burkitt's lymphoma cells; HG-3 (DSMZ # ACC765), and CII (DSMZ # ACC773) are a chronic lymphocytic leukemia cell line;

Su-DHL 6 (DSMZ # ACC572), U2932 (DSMZ # ACC633) and OCI-LY7 (DSMZ # ACC688) are a Diffuse large B-cell lymphoma (DLBCL) cell line; JVM-2 (ATCC® CRL-3002) is a mantle cell lymphoma cell line; and BALL-1 (DSMZ # ACC742) is an acute lymphoblastic leukemia cell line.

Culture conditions of cell lines used are according to supplier's information.

Cell Medium: Iscove's Modified Dulbecco's Medium (IMDM), Invitrogen, Cat No.: 31980-048; RPMI1640, Invitrogen, Cat No.: 31870-074; GlutaMAX, Invitrogen, CAT No.: 35050-38 LOT No.: 1504647; FCS: Sigma CAT No.: F7524 LOT No.: 111M3396.

NKs: RPM11640, with GlutaMAX™, Invitrogen, Cat No.: 31870-074, 10% FCS; Biocoll: Biochrome AG CAT No.: L6115 LOT No.: 0034D; MACS NK cell isolation kit: Miltenyi Biotec CAT No.: 130-092-657 LOT No.: 5150130115; Ibrutinib: Selleck Chem LOT No.: S2680; FCS: Sigma CAT No.: F7524 LOT No.: 111M3396; and RefmAb33 (anti-RSV) with same Fc region as MOR00208.

Methods

The cytotoxicity of MOR00208 and Ibrutinib alone and in combination were tested in the MEC-1 cell line (CLL). The cytotoxicity of MOR00208 and Ibrutinib alone and in combination are tested in the following target cell lines: JVM-2, Ramos, HG-3, CII, Su-DHL 6, U2932, OCI-LY7, JVM-2 and BALL-1.

Ibrutinib is a covalent inhibitor of Bruton's tyrosine kinase and should abrogate proliferation in target cell lines. MOR00208 targets CD19 and mediates target cell killing via ADCC. Target cell killing is measured using the following parameters: Ibrutinib at a concentration range of between 0.033 and 33 μM, specifically at 0.3 μM, 1.0 μM and 3.0 μM; MOR00208 at a concentration range from 0.001-10 nM, specifically at 0.01 nM, 0.1 nM, and 10 nM, and the combination of MOR00208 and Ibrutinib. The following are used as controls: RefmAb33 or NK cells alone. In the Ibrutinib group as well as in the MOR00208+Ibrutinib combination group, target cells are pre-treated with Ibrutinib for 7 days prior to the ADCC assay measurements. The target cells are counted and stained using 1 μg/ml CFSE end concentration. For DMSO treated target cells, an effector: target (E:T) ratio of 2:1 is chosen, corresponding to a cell density of $5 \times 10^5$/ml. The proliferative effect on target cells caused by Ibrutinib treatment was included by adjusting the E:T ratio in inhibitor treated cells. The NK cells are counted and adjusted to $1 \times 10^6$/ml. The target cell killing assays were performed as follows: using 96 well plates, 100 μl of target cell suspension was added per well, followed by 100 μl cell suspension of NK cells to each well resulting in an E:T ratio of 2:1. The antibodies were diluted in a range of 10-0.001 nM in medium. Cells were centrifuged and target: effector cell-pellets were re-suspended in 100 μl antibody-containing medium or the according control solution. The assay was incubated for 4 h in CO2-incubator at 37° C. After 10 min incubation on ice, 50 μl DAPI solution was added to each well (final concentration 1 μg/ml) and incubated on ice for 10 min. The cell killing measurements were performed with FACS-Verse. Dead target cells were DAPI positive.

Figure 2:
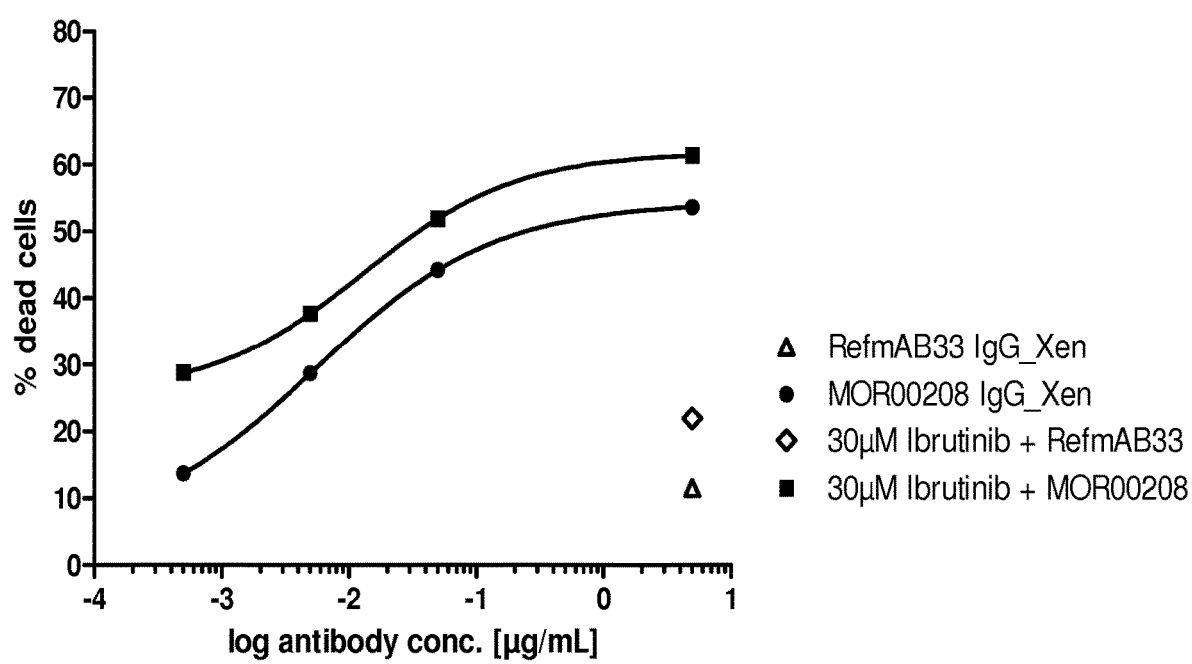
FIG. 2 shows the cytotoxicity effects of MOR00208 and Ibrutinib alone and in combination on MEC-1 cells. MEC-1 cells were pre-treated with 30 µM Ibrutinib for 24 hours.
Figure 3:
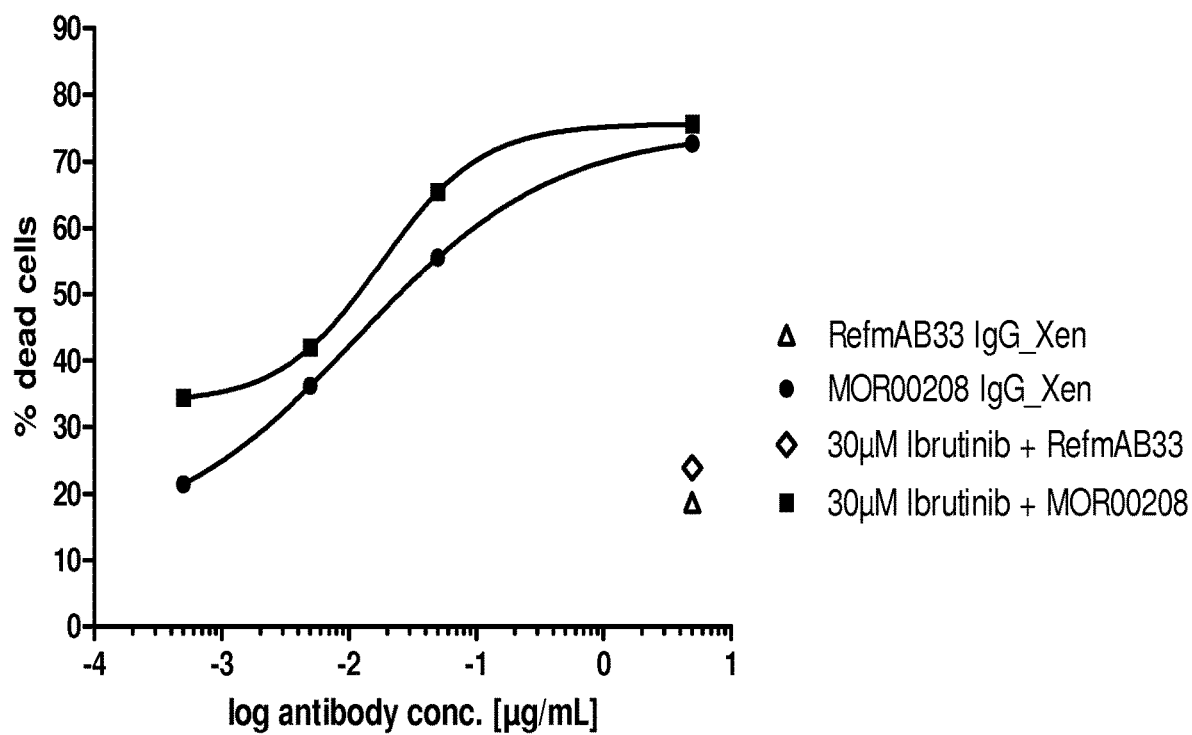
FIG. 3 shows the cytotoxicity effects of MOR00208 and Ibrutinib alone and in combination on MEC-1 cells. MEC-1 cells were pre-treated with 30 µM Ibrutinib for 24 hours.

Pre-experiments following the methods described above were completed with both MEC-1 cells and RAMOS cells. FIGS. 1-3 show the results of the pre-experiments.

Data

Figure 6:
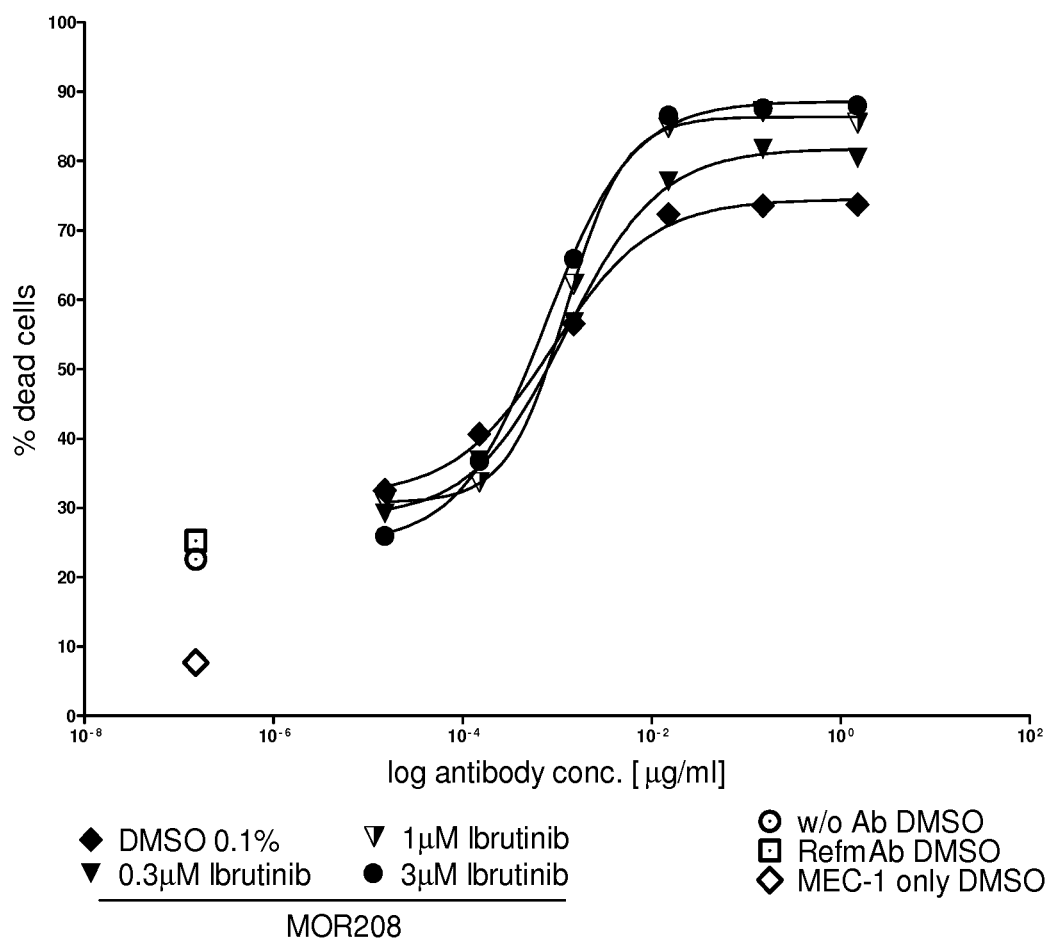
FIGS. 6-8 show the cytotoxicity of MOR00208 and Ibrutinib alone and in combination in MEC-1 cell line.
Figure 7:
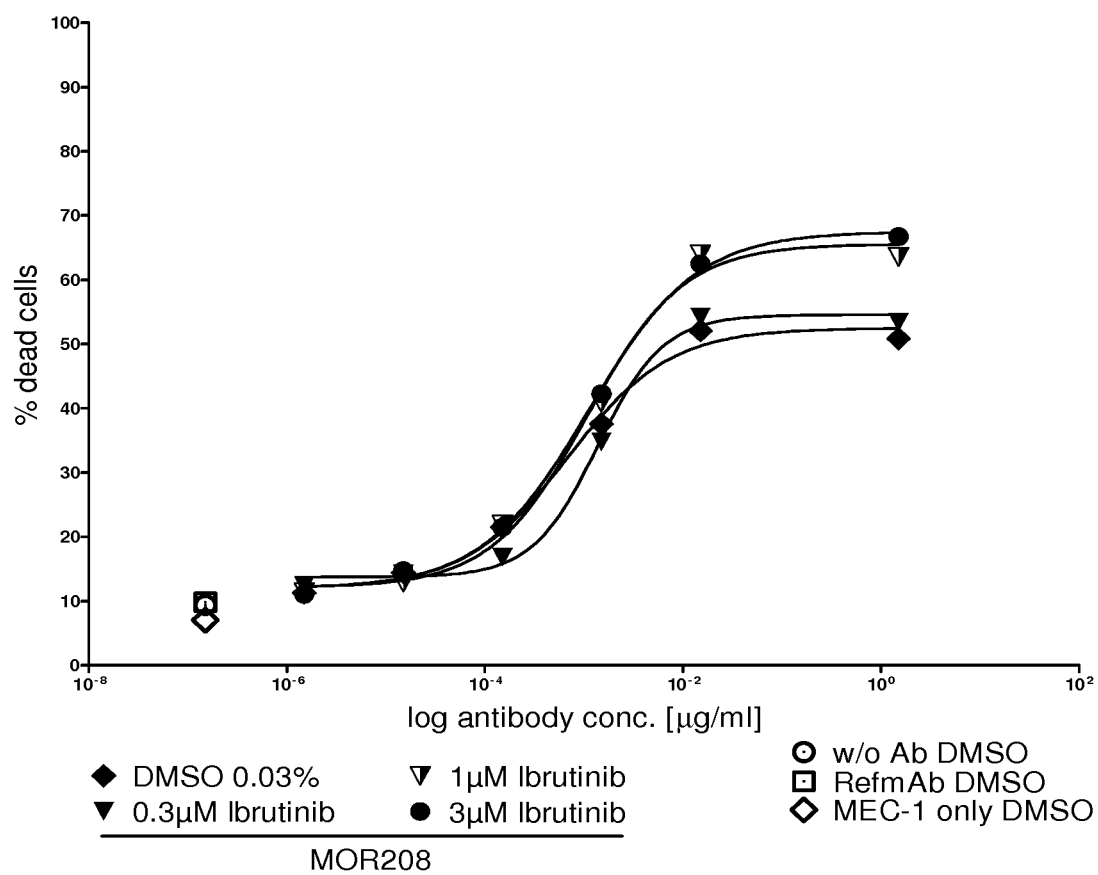
Figure 8:
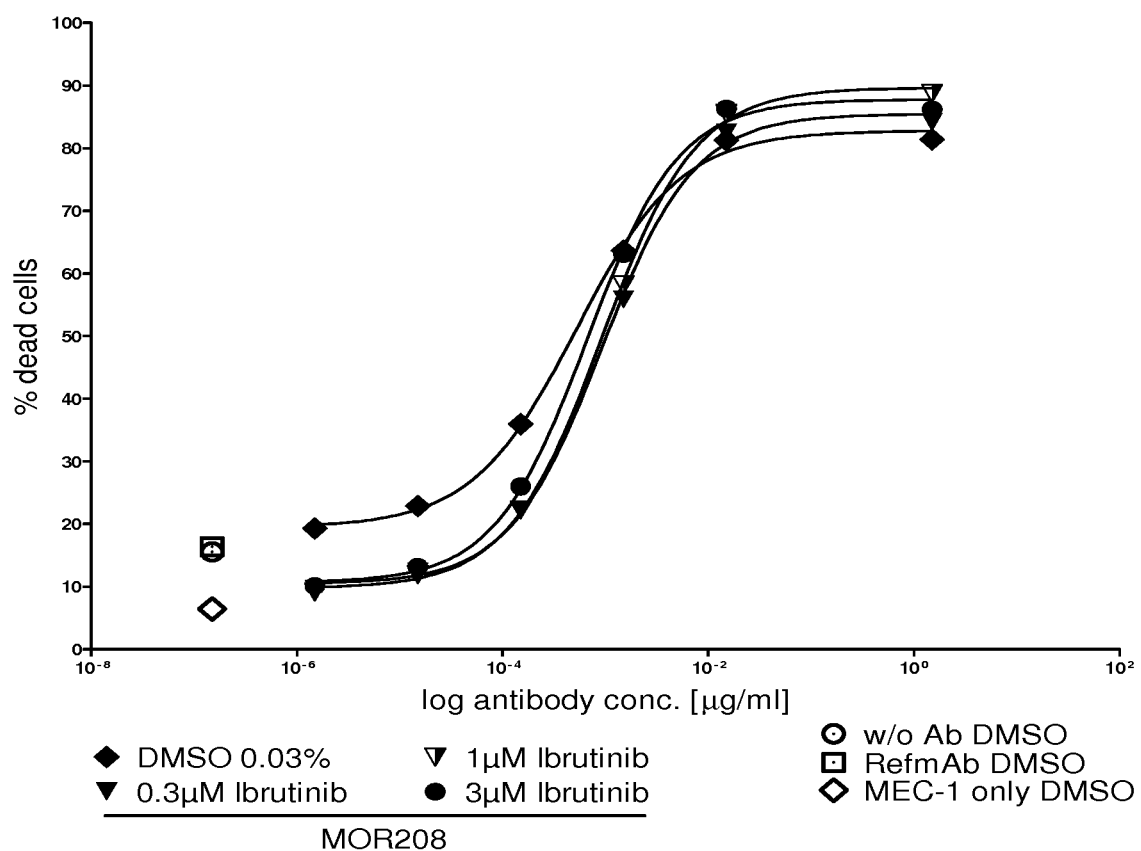

In total, three experiments were performed in order to determine the mediation of ADCC on MEC-1 cells by the combination of MOR00208 and Ibrutinib. The ADCC dose response curves for Experiments 1-3 are shown in FIGS. 6-8.

The percent (%) dead cells (raw data) for Experiments 1-3 are shown in Tables 1-9 below.

Experiment 1:

TABLE 1

Ibrutinib at 3 μM

| | MOR00208 Concentration | | |
|---|---|---|---|
| | 10 nM | 0.1 nM | 0.01 nM |
| A: MOR00208 alone | 73.77 | 72.31 | 56.54 |
| B: Ibr alone 3 μM | 17.07 | 17.07 | 17.07 |
| C: control (0.1% DMSO/Ref33) | 25.27 | 25.27 | 25.27 |
| AB: combination | 88.01 | 86.59 | 65.89 |

TABLE 2

Ibrutinib at 1 μM

| | MOR00208 Concentration | | |
|---|---|---|---|
| | 10 nM | 0.1 nM | 0.01 nM |
| A: MOR00208 alone | 73.77 | 72.31 | 56.54 |
| B: Ibr alone 1 μM | 24.33 | 24.33 | 24.33 |
| C: control (0.1% DMSO/Ref33) | 25.27 | 25.27 | 25.27 |
| AB: combination | 85.48 | 84.83 | 62.22 |

TABLE 3

Ibrutinib at 0.3 μM

| | MOR00208 Concentration | | |
|---|---|---|---|
| | 10 nM | 0.1 nM | 0.01 nM |
| A: MOR00208 alone | 73.77 | 72.31 | 56.54 |
| B: Ibr alone 0.3 μM | 21.99 | 21.99 | 21.99 |
| C: control (0.1% DMSO/Ref33) | 25.27 | 25.27 | 25.27 |
| AB: combination | 80.51 | 77.08 | 56.79 |

Experiment 2:

TABLE 4

Ibrutinib at 3 μM

| | MOR00208 Concentration | | |
|---|---|---|---|
| | 10 nM | 0.1 nM | 0.01 nM |
| A: MOR00208 alone | 50.83 | 52.10 | 37.57 |
| B: Ibr alone 3 μM | 10.84 | 10.84 | 10.84 |
| C: control (0.03% DMSO/Ref33) | 9.81 | 9.81 | 9.81 |
| AB: combination | 66.70 | 62.47 | 42.25 |

TABLE 5

Ibrutinib at 1 μM

| | MOR00208 Concentration | | |
|---|---|---|---|
| | 10 nM | 0.1 nM | 0.01 nM |
| A: MOR00208 alone | 50.83 | 52.10 | 37.57 |
| B: Ibr alone 1 μM | 8.39 | 8.39 | 8.39 |
| C: control (0.03% DMSO/Ref33) | 9.81 | 9.81 | 9.81 |
| AB: combination | 63.56 | 63.97 | 40.84 |

TABLE 6

Ibrutinib at 0.3 μM

| | MOR00208 Concentration | | |
|---|---|---|---|
| | 10 nM | 0.1 nM | 0.01 nM |
| A: MOR00208 alone | 50.83 | 52.10 | 37.57 |
| B: Ibr alone 0.3 μM | 8.56 | 8.56 | 8.56 |
| C: control (0.03% DMSO/Ref33) | 9.81 | 9.81 | 9.81 |
| AB: combination | 53.41 | 54.22 | 34.83 |

Experiment 3:

TABLE 7

Ibrutinib at 3 μM

| | MOR00208 Concentration | | |
|---|---|---|---|
| | 10 nM | 0.1 nM | 0.01 nM |
| A: MOR00208 alone | 81.41 | 81.30 | 63.68 |
| B: Ibr alone 3 μM | 8.26 | 8.26 | 8.26 |
| C: control (0.03% DMSO/Ref33) | 16.40 | 16.40 | 16.40 |
| AB: combination | 86.19 | 86.35 | 63.10 |

TABLE 8

Ibrutinib at 1 μM

| | MOR00208 Concentration | | |
|---|---|---|---|
| | 10 nM | 0.1 nM | 0.01 nM |
| A: MOR00208 alone | 81.41 | 81.30 | 63.68 |
| B: Ibr alone 1 μM | 7.50 | 7.50 | 7.50 |
| C: control (0.03% DMSO/Ref33) | 16.40 | 16.40 | 16.40 |
| AB: combination | 88.75 | 85.58 | 58.17 |

TABLE 9

Ibrutinib at 0.3 μM

| | MOR00208 Concentration | | |
|---|---|---|---|
| | 10 nM | 0.1 nM | 0.01 nM |
| A: MOR00208 alone | 81.41 | 81.30 | 63.68 |
| B: Ibr alone 0.3 μM | 8.56 | 8.56 | 8.56 |
| C: control (0.03% DMSO/Ref33) | 16.40 | 16.40 | 16.40 |
| AB: combination | 84.17 | 82.49 | 55.89 |

Calculation of Synergism

The raw data (% dead cells) are analyzed as follows: 1) from the raw data (% dead cells), the background (controls) are subtracted, resulting in the specific killing for each treatment group; then 2) the specific killing values are normalized by setting the combination of MOR00208+Ibrutinib to 1.

Combination Index (CI) calculations are completed in order to determine synergy of the combination of the exemplified anti-CD19 antibody and Ibrutinib as compared to MOR00208 and Ibrutinib alone. Such calculations are described in Ting-Chao Chou, Theoretical Basis, Experimental Design, and Computerized Simulation of Synergism and Antagonism in Drug Combination Studies, Pharmacol Rev 58:621-681 (2006), which is incorporated by reference in its entirety and Chou T C, Talalay P, Quantitative analysis of dose-effect relationships: the combined effects of multiple drugs or enzyme inhibitors. Adv Enzyme Regul 22: 27-55 (1984), which is incorporated by reference in its entirety. The methods of Chou-Talalay are carried out using the CI-isobol method.

Median Effect Equation

The median-effect equation models the effect of an inhibitor (such as a drug) as $F_a/F_u=(D/D50)^m$, where D is the dose, $F_a$ and $F_u$ is the fraction of the system affected and unaffected by the dose D ($F_a+F_u=1$); D50 is the dose producing the median effect (e.g. IC50, ED50, LD50). The constant m determines the shape of the dose-effect curve. We use GraphPad Prism to carry out a nonlinear regression calculation to estimate the parameters m and D50.

CI-Isobol Method

The CI-isobol method provides a quantitative assessment of synergism between drugs. A combination index (CI) is estimated from dose-effect data of single and combined drug treatments. A value of CI less than 1 indicates synergism; CI=1 indicates additive effect; and CI>1 indicates antagonism. Drug interaction (synergism or antagonism) is more pronounced the farther a CI value is from 1.

Formally, the combination index (CI) of a combined drug treatment is defined as $$CI=D_1/D_{x1}+D_2/D_{x2}$$

Here D1 and D2 are the doses of drug 1 and drug 2 of the combination, respectively; and Dx1, and Dx2 is the dose of a treatment with only drug 1 and drug 2 that would give the same effect as that of the combination. The doses Dx1 and Dx2 need to be estimated from the dose-effect data of single drug treatments. Essentially, a median effect equation is fitted to the data of each drug. From the median effect equation of a drug, we can estimate the dose (i.e. D) necessary to produce an effect (i.e. Fa, Fu). The further a point lies from the additive line, the bigger the different between 1 and its CI, thus the stronger the (synergistic or antagonistic) effect is.

Results

Figure 9:
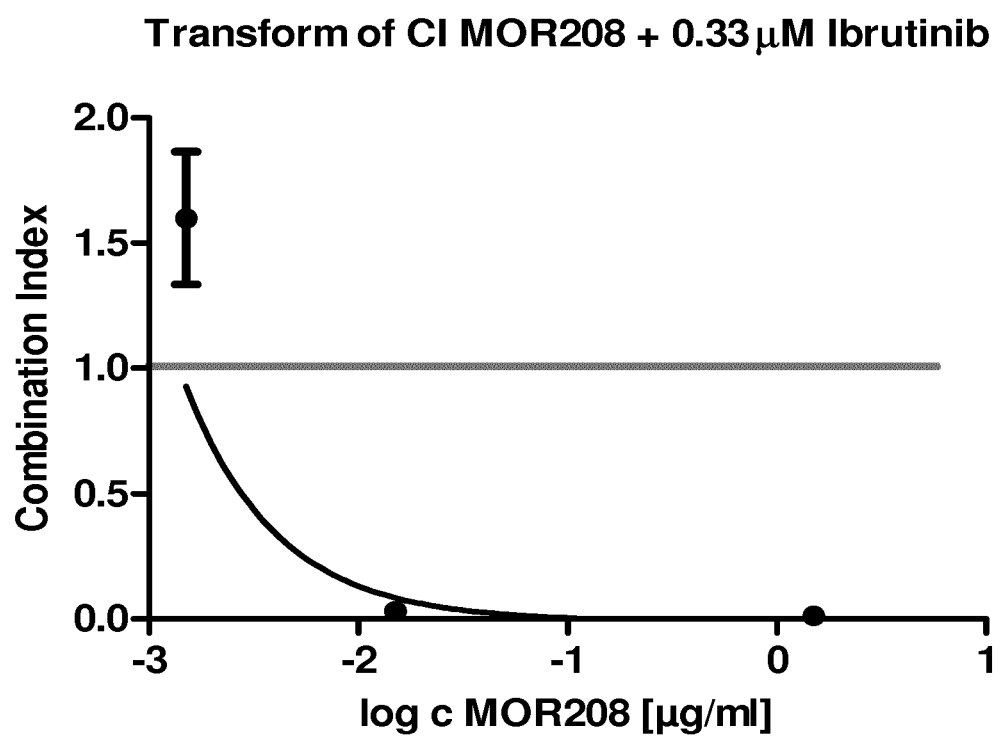
FIGS. 9-11 show Chou-Talay Combination Index curves of MOR00208 and Ibrutinib in combination in MEC-1 cell line.
Figure 10:
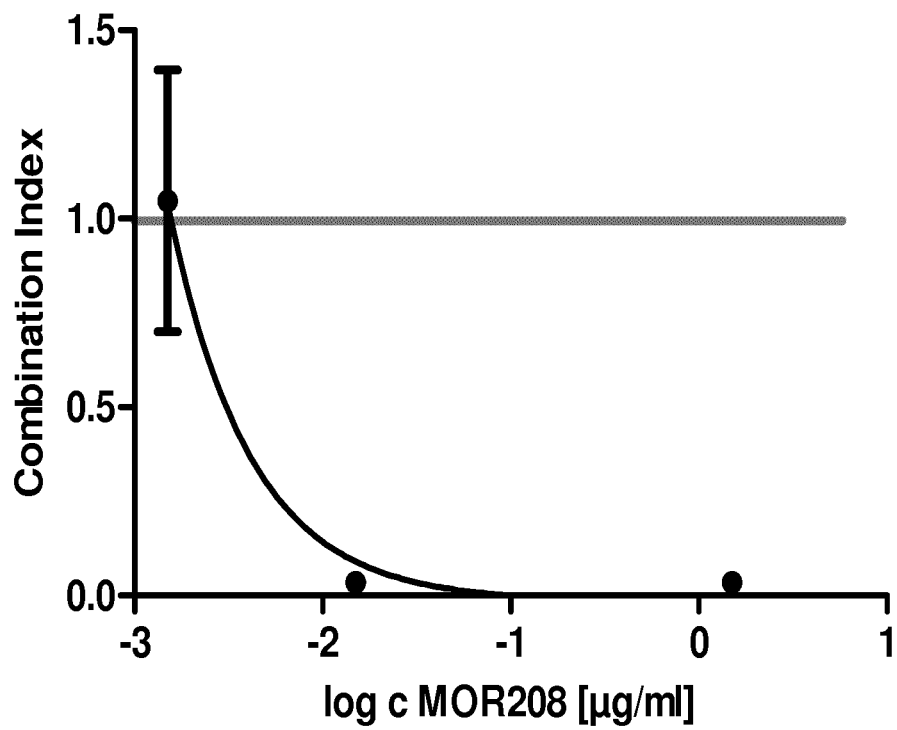
Figure 11:
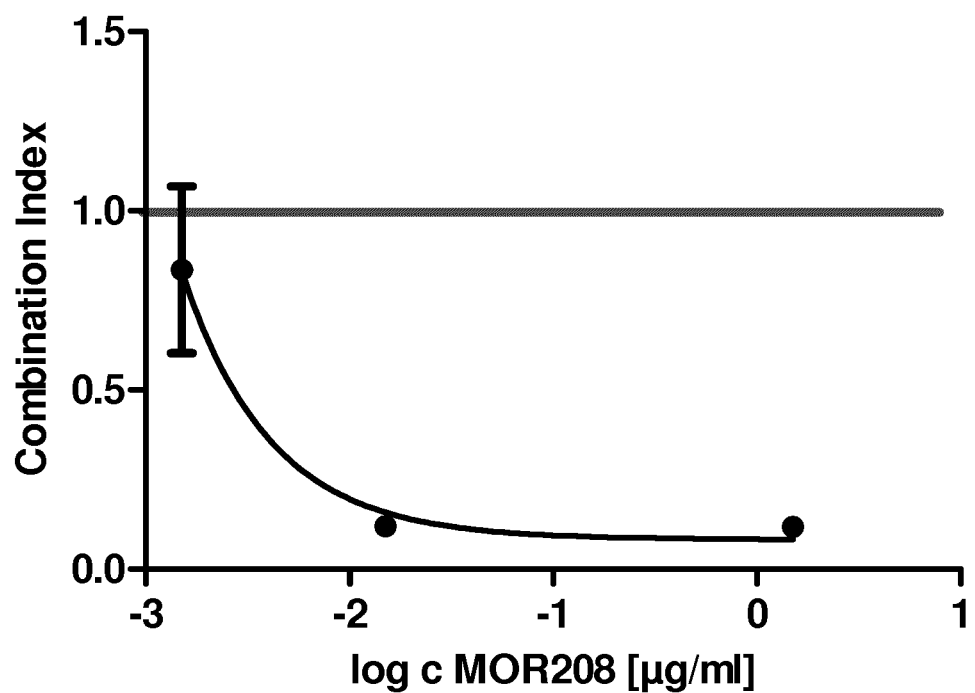

The Chou index curves are shown in FIGS. 9-11. Data from the three experiments (at the same concentrations) was merged to produce one curve for each Ibrutniib concentration.

The Chou index values indicate clear synergism of the combination of MOR00208 and Ibrutinib in the specific killing of MEC-1 cells as compared to MOR00208 and Ibrutinib alone.

Therefore, the combination of MOR00208 and Ibrutinib will also behave synergistically in the treatment of non-Hodgkin's lymphoma (NHL), chronic lymphoid leukemia (CLL), and acute lymphoblastic leukemia (ALL) in humans.

Additional Analysis

Another approach to calculate and compare effects of single agents when used in combination is the fractional product concept first described by Webb J. L. in "Enzymes and metabolic inhibitors" in 1963. This analysis method considers that effects of several drugs can be directed against the same cell fraction, as long as the effects are mutually non-exclusive, which is true for MOR00208 and Ibrutinib, and therefore the measured combination effect will be less as the theoretical summation of the single effects. The fractional product concept claims, whenever two drugs kill 50% of a target cell fraction the effect in combination would only be 75% (applied equation: 1−(1−0.5)×(1−0.5)=0.75) and not the expected 100%, due to only 50% of the target cells still being viable and susceptible to one of the two drugs.

Another approach to calculate and compare effects of single agents when used in combination is the approach of Clarke et al., Issues in experimental design and endpoint analysis in the study of experimental cytotoxic agents in vivo in breast cancer and other models, Breast Cancer Research and Treatment 46:255-278 (1997), which is incorporated by reference in its entirety.

The % dead cells (raw data) from Tables 1-16 was analysed in the following way:

Antagonistic $(AB)/C < (A/C) \times (B/C)$

Additive $(AB)/C = (A/C) \times (B/C)$

Synergistic $(AB)/C > (A/C) \times (B/C)$ where A is the treatment with MOR00208 alone; B is the treatment with Ibrutinib alone; C is response to the control DMSO+RefMab33; AB is the combination of treatments A and B.

Experiment 1

TABLE 10

Clarke analysis of Data shown in Table 1

| | MOR00208 Concentration | | |
|---|---|---|---|
| | 10 nM | 0.1 nM | 0.01 nM |
| (AB)/C | 3.48 | 3.43 | 2.61 |
| (A/C) × (B/C) | 1.97 | 1.93 | 1.51 |

Figure 12:
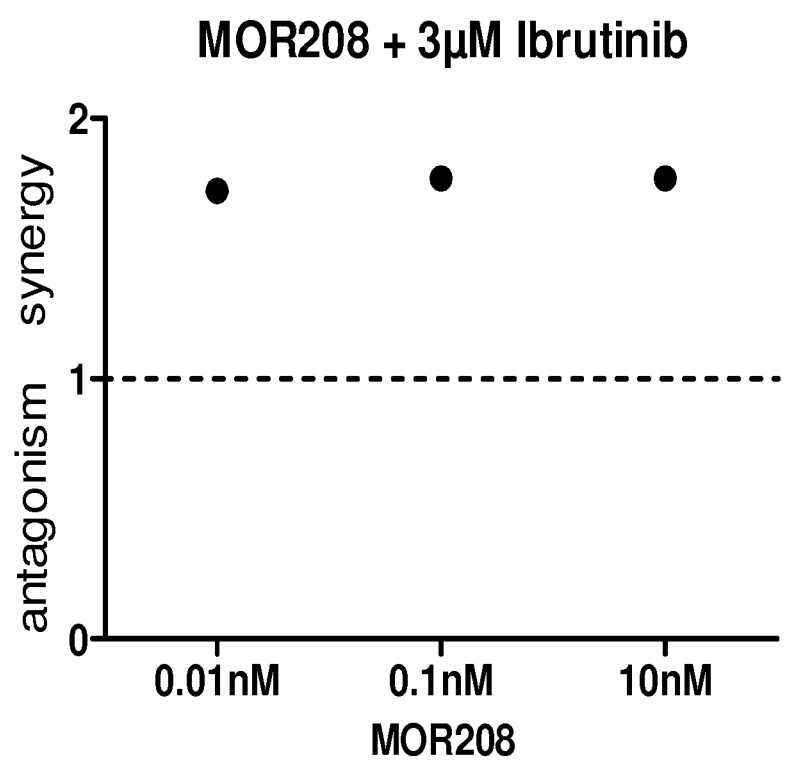
FIGS. 12-20 show the Clarke et al. synergy calculations of MOR00208 and Ibrutinib in combination in MEC-1 cell line.

This Clarke analysis of the data shown in Table 1 is also graphically represented in FIG. 12.

TABLE 11

Clarke analysis of Data shown in Table 2

| | MOR00208 Concentration | | |
|---|---|---|---|
| | 10 nM | 0.1 nM | 0.01 nM |
| (AB)/C | 3.38 | 3.36 | 2.46 |
| (A/C) × (B/C) | 2.81 | 2.76 | 2.15 |

Figure 13:
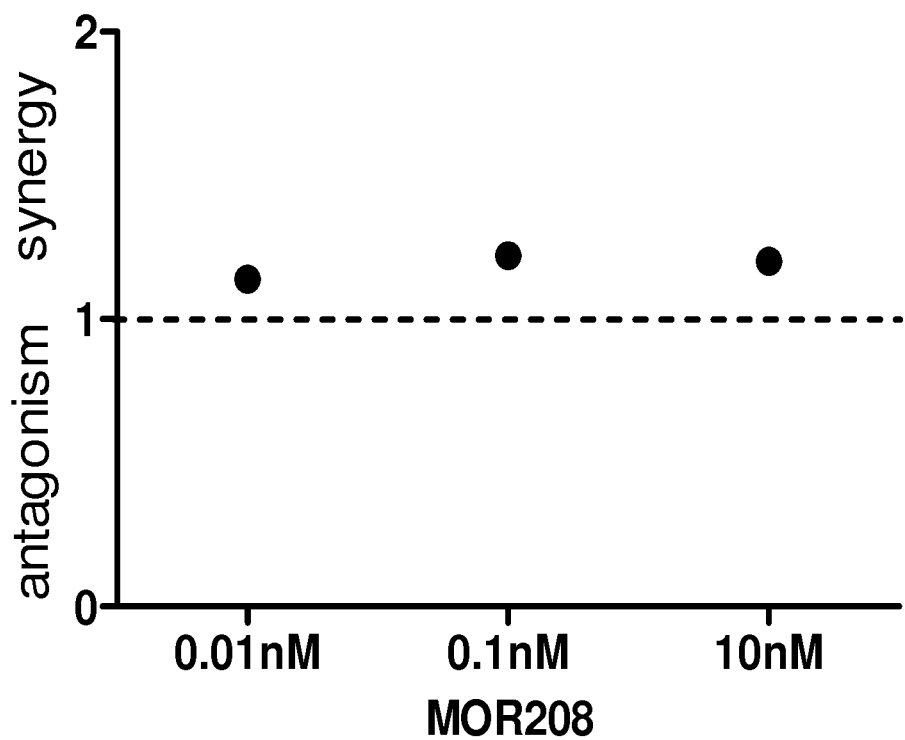

This Clarke analysis of the data shown in Table 2 is also graphically represented in FIG. 13.

TABLE 12

Clarke analysis of Data shown in Table 3

| | MOR00208 Concentration | | |
|---|---|---|---|
| | 10 nM | 0.1 nM | 0.01 nM |
| (AB)/C | 3.19 | 3.05 | 2.25 |
| (A/C) × (B/C) | 2.54 | 2.49 | 1.95 |

Figure 14:
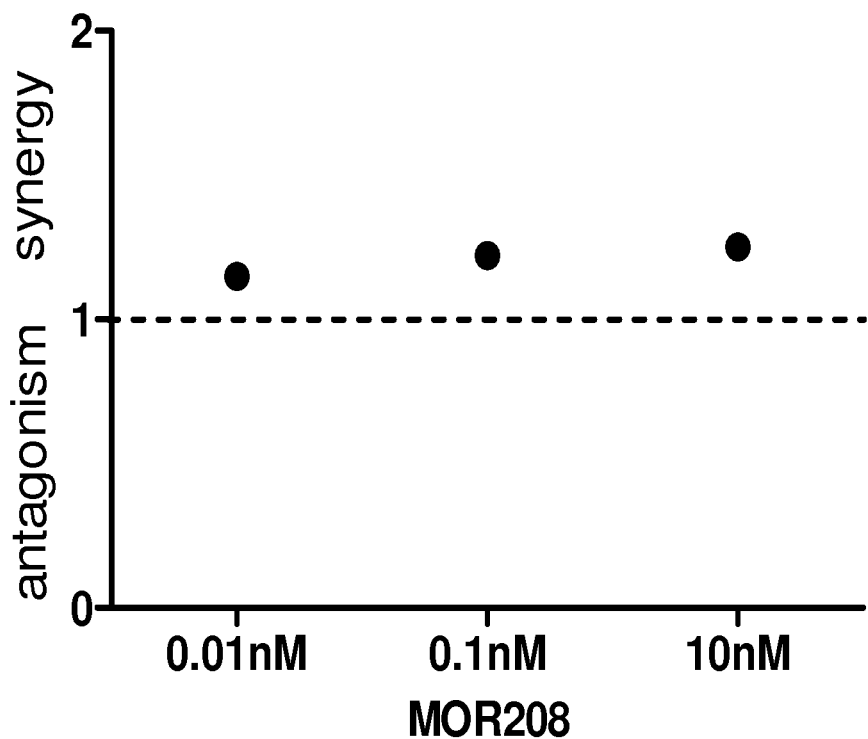

This Clarke analysis of the data shown in Table 3 is also graphically represented in FIG. 14.

Experiment 2

TABLE 13

Clarke analysis of Data shown in Table 4

| | MOR00208 Concentration | | |
|---|---|---|---|
| | 10 nM | 0.1 nM | 0.01 nM |
| (AB)/C | 6.80 | 6.37 | 4.31 |
| (A/C) × (B/C) | 5.73 | 5.87 | 4.23 |

Figure 15:
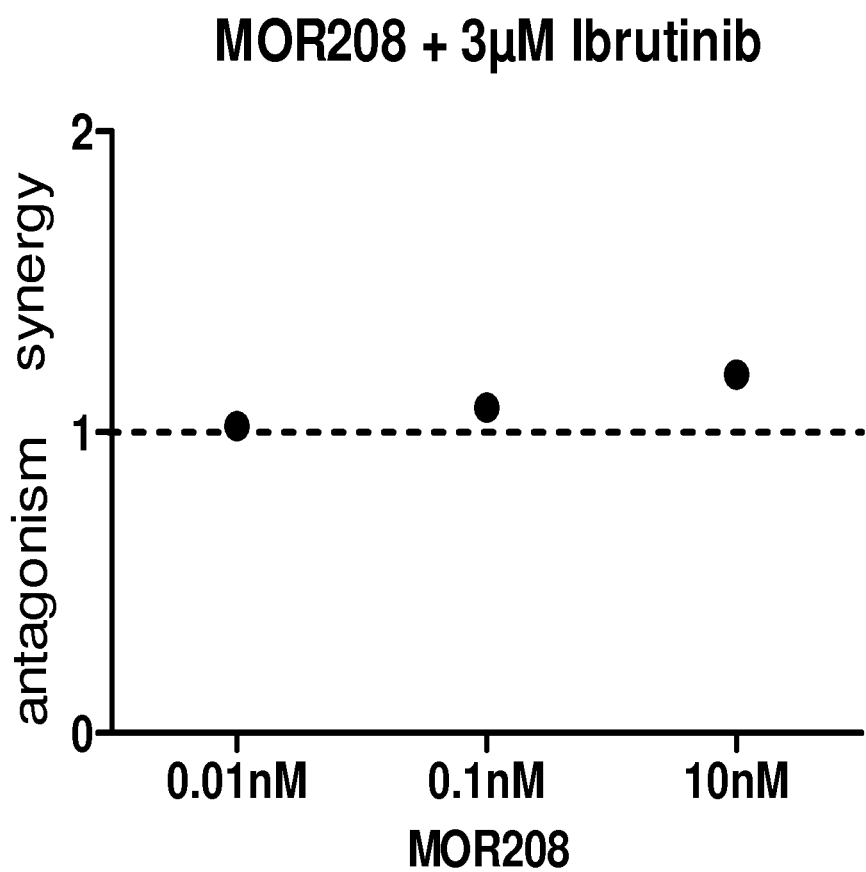

This Clarke analysis of the data shown in Table 4 is also graphically represented in FIG. 15.

TABLE 14

Clarke analysis of Data shown in Table 5

| | MOR00208 Concentration | | |
|---|---|---|---|
| | 10 nM | 0.1 nM | 0.01 nM |
| (AB)/C | 6.48 | 6.52 | 4.16 |
| (A/C) × (B/C) | 4.43 | 4.54 | 3.27 |

Figure 16:
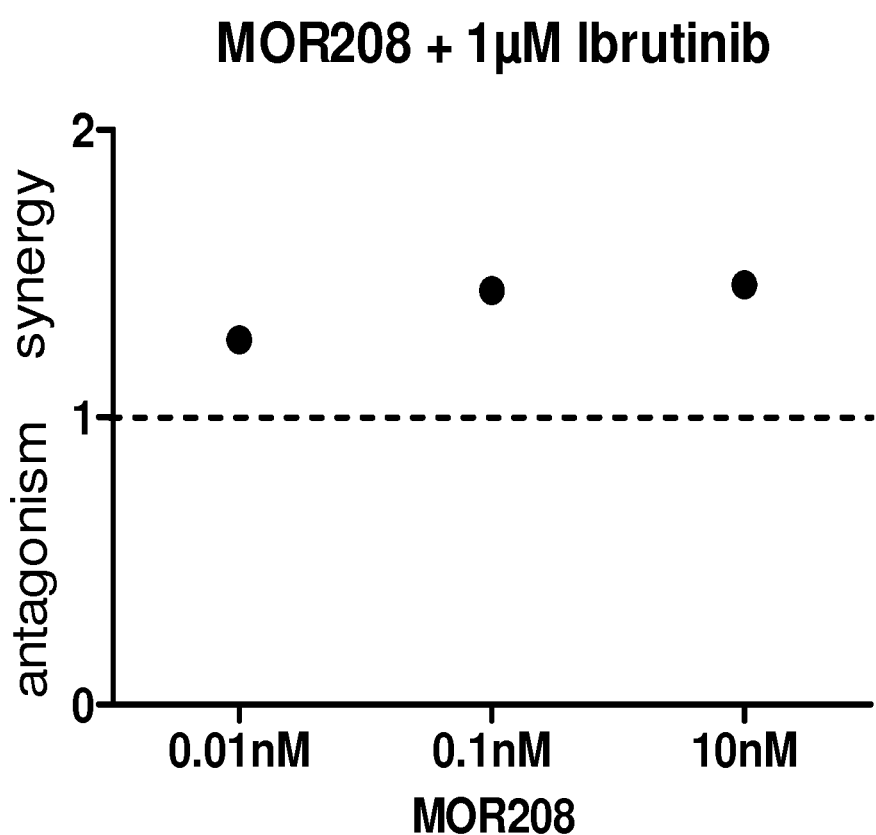

This Clarke analysis of the data shown in Table 5 is also graphically represented in FIG. 16.

TABLE 15

Clarke analysis of Data shown in Table 6

| | MOR00208 Concentration | | |
|---|---|---|---|
| | 10 nM | 0.1 nM | 0.01 nM |
| (AB)/C | 5.44 | 5.53 | 3.55 |
| (A/C) × (B/C) | 4.52 | 4.63 | 3.34 |

Figure 17:
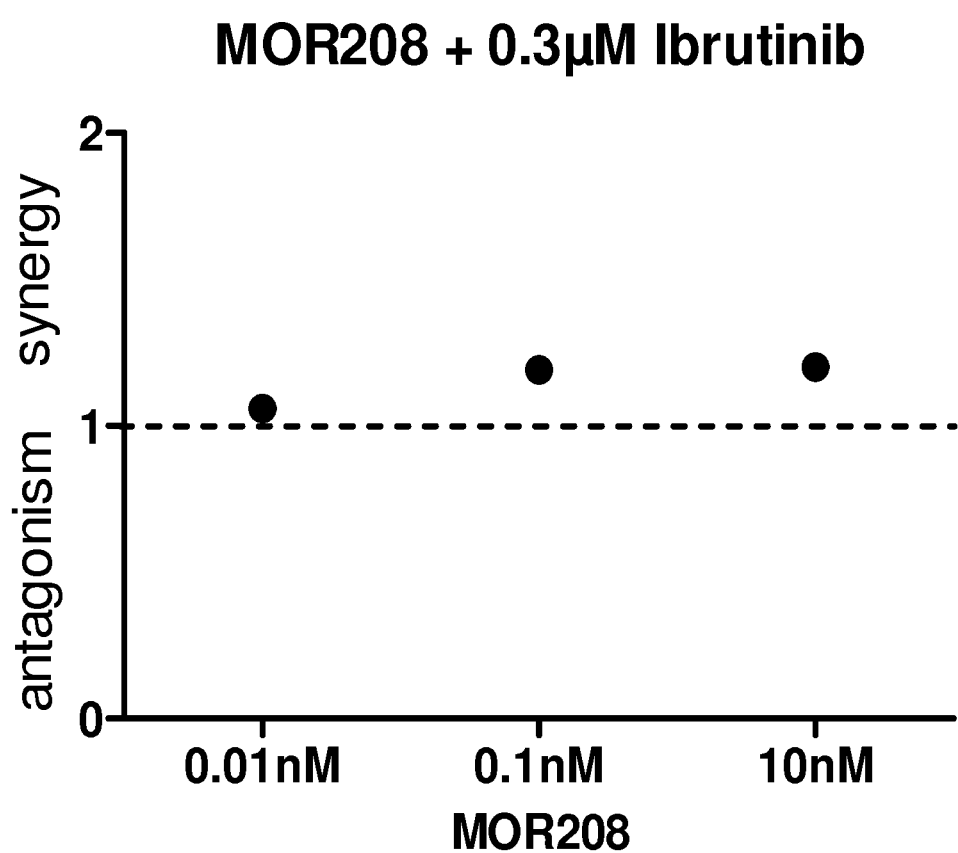

This Clarke analysis of the data shown in Table 6 is also graphically represented in FIG. 17.

Experiment 3

TABLE 16

Clarke analysis of Data shown in Table 7

| | MOR00208 Concentration | | |
|---|---|---|---|
| | 10 nM | 0.1 nM | 0.01 nM |
| (AB)/C | 5.26 | 5.26 | 3.85 |
| (A/C) × (B/C) | 2.50 | 2.50 | 1.95 |

Figure 18:
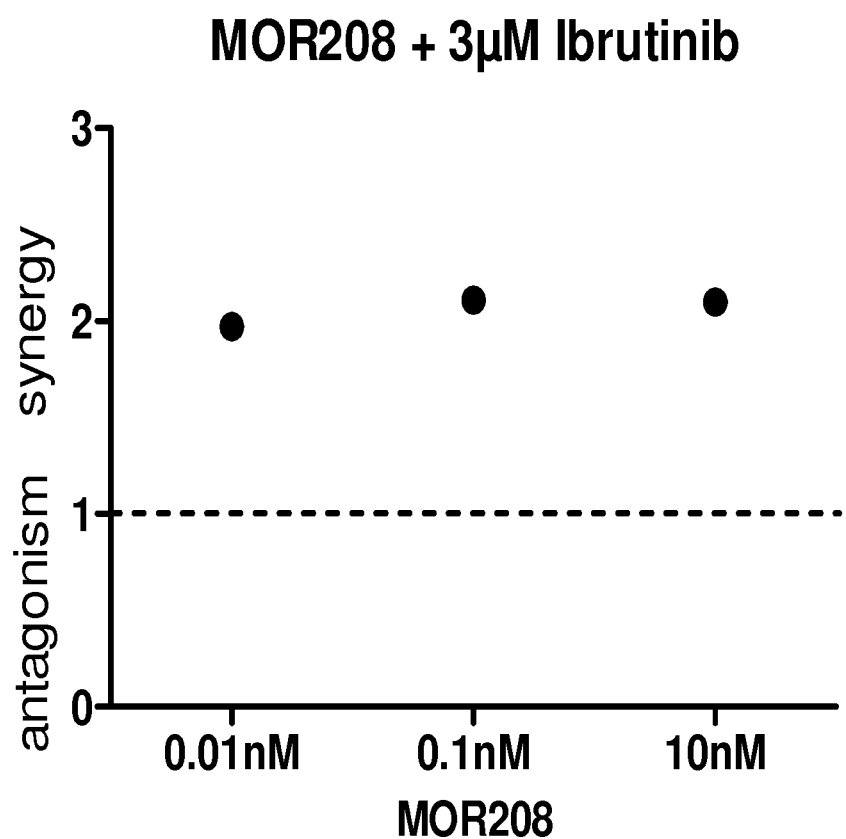

This Clarke analysis of the data shown in Table 7 is also graphically represented in FIG. 18.

TABLE 17

Clarke analysis of Data shown in Table 8

| | MOR00208 Concentration | | |
|---|---|---|---|
| | 10 nM | 0.1 nM | 0.01 nM |
| (AB)/C | 5.41 | 5.22 | 3.55 |
| (A/C) × (B/C) | 2.27 | 2.27 | 1.78 |

Figure 19:
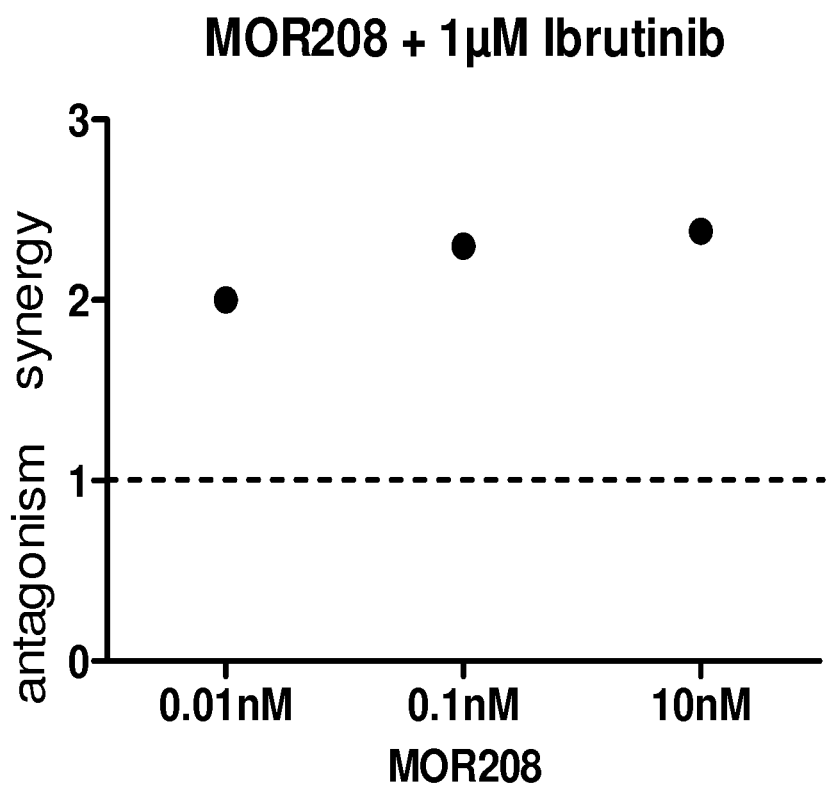

This Clarke analysis of the data shown in Table 8 is also graphically represented in FIG. 19.

TABLE 18

Clarke analysis of Data shown in Table 9

| | MOR00208 Concentration | | |
|---|---|---|---|
| | 10 nM | 0.1 nM | 0.01 nM |
| (AB)/C | 5.13 | 5.03 | 3.41 |
| (A/C) × (B/C) | 2.59 | 2.59 | 2.03 |

Figure 20:
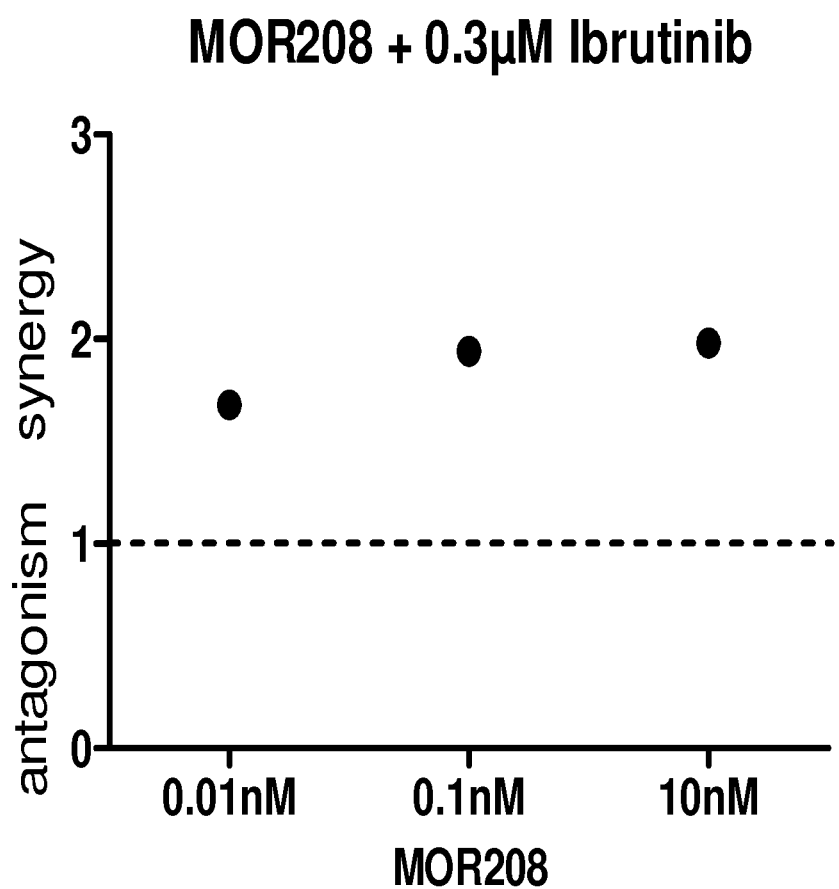

This Clarke analysis of the data shown in Table 9 is also graphically represented in FIG. 20.

Results of Clarke

Experiments 1-3 at each concentration showed clear synergy of the combination of MOR00208+Ibrutinib using the methods of Clarke et al. The methods of Clarke et al., however, show synergism despite in a few experiments where the Ibrutinib activity was less than that of the control.

It is to be understood that the description, specific examples and data, while indicating exemplary embodiments, are given by way of illustration and are not intended to limit the present invention. Various changes and modifications within the present invention will become apparent to the skilled artisan from the discussion, disclosure and data contained herein, and thus are considered part of the invention.

We claim:

1. A synergistic combination for treatment of non-Hodgkin's lymphoma, chronic lymphocytic leukemia and/or acute lymphoblastic leukemia, said composition comprising an antibody specific for CD19 wherein said antibody comprises an HCDR1 region of sequence SYVMH (SEQ ID NO: 1), an HCDR2 region of sequence NPYNDG (SEQ ID NO: 2), an HCDR3 region of sequence GTYYYGTRVFDY (SEQ ID NO: 3), an LCDR1 region of sequence RSSKSLQNVNGNTYLY (SEQ ID NO: 4), an LCDR2 region of sequence RMSNLNS (SEQ ID NO: 5), and an LCDR3 region of sequence MQHLEYPIT (SEQ ID NO: 6) and Ibrutinib.

2. A combination according to claim 1, wherein the antibody comprises a variable heavy chain of the sequence EVQLVESGGGLVKPGGSLKLSCAASGYTFTSYVMHWVRQAPGKGLEWIGYINPY NDGTKYNEKFQGRVTISSDKSISTAYMELSSLRSEDTAMYYCARGTYYYGTRVFDYWG QGTLVTVSS (SEQ ID NO: 10) and a variable light chain of the sequence DIVMTQSPATLSLSPGERATLSCRSSKSLQNVNGNTYLYWFQQKPGQSPQLLIYR MSNLNSGVPDRFSGSGSGTEF TLTISSLEPEDFAVYYCMQHLEYPITFGAGTKLEIK (SEQ ID NO: 11).

3. A combination according to claim 1, wherein the antibody comprises a heavy chain constant domain of the sequence

```
                                              (SEQ ID NO: 12)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPDVFLFPPKPKDTLMISRTPEVTCVVVDVS

HEDPEVQFNWYVDGVEVHNAKTKPREEQFNSTFRVVSVLTVVHQDWLNGK

EYKCKVSNKALPAPEEKTISKTKGQPREPQVYTLPPSREEMTKNQVSLTC

LVKGFYPSDIAVEWESNGQPENNYKTTPPMLDSDGSFFLYSKLTVDKSRW

QQGNVFSCSVMHEALHNHYTQKSLSLSPGK.
```

4. A combination according to claim 1, wherein the antibody comprises a light chain constant domain of the sequence

```
                                              (SEQ ID NO: 13)
RTVAAPSVFIFPPSDEQLKSGTASVVCLLNNFYPREAKVQWKVDNALQSG

NSQESVTEQDSKDSTYSLSSTLTLSKADYEKHKVYACEVTHQGLSSPVTK

SFNRGEC.
```

5. A method for treatment of chronic lymphocytic leukemia, acute lymphoblastic leukemia or non-Hodgkin's lymphoma in a patient, said method comprising administering the combination of claim 1 to the patient.

6. The method according to claim 5 for use in the treatment of non-Hodgkin's lymphoma, wherein the non-Hodgkin's lymphoma is selected from the group consisting of follicular lymphoma, small lymphocytic lymphoma, mucosa-associated lymphoid tissue, marginal zone, diffuse large B cell, Burkitt's, and mantle cell.

7. The method according to claim 6, wherein the non-Hodgkin's lymphoma is follicular lymphoma.

8. The method according to claim 6, wherein the non-Hodgkin's lymphoma is small lymphocytic lymphoma.

9. The method according to claim 6, wherein the non-Hodgkin's lymphoma is mucosa-associated lymphoid tissue.

10. The method according to claim 6, wherein the non-Hodgkin's lymphoma is diffuse large B cell lymphoma.

11. The method according to claim 6, wherein the non-Hodgkin's lymphoma is Burkitt's lymphoma.

12. The method according to claim 6, wherein the non-Hodgkin's lymphoma is mantle cell lymphoma.

13. The method according to claim 5, wherein the antibody specific for CD19 and the Ibrutinib of said combination are administered separately.

14. The method of claim 5, wherein the Ibrutinib of said combination is administered prior to administration of the antibody specific for CD19.

15. The method of claim 5, wherein the antibody specific for CD19 and the Ibrutinib of said combination are administered simultaneously.

16. The method of claim 5, wherein the antibody specific for CD19 and the Ibrutinib of said combination are administered at a time where both drugs are active in the patient at the same time.

* * * * *